(12) United States Patent
Bach et al.

(10) Patent No.: US 7,183,304 B2
(45) Date of Patent: Feb. 27, 2007

(54) HETEROCYCLIC COMPOUNDS AND METHODS OF USE

(75) Inventors: Andrew Thomas Bach, Summit, NJ (US); Prasad Koteswara Kapa, Parsippany, NJ (US); George Tien-San Lee, Towaco, NJ (US); Eric M. Loesser, Scotch Plains, NJ (US); Michael Lloyd Sabio, Randolph, NJ (US); James Lawrence Stanton, Charlestown, MA (US); Thalaththani Ralalage Vedananda, Shrewsbury, MA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 10/495,992

(22) PCT Filed: Nov. 20, 2002

(86) PCT No.: PCT/EP02/13025

§ 371 (c)(1),
(2), (4) Date: Jun. 14, 2004

(87) PCT Pub. No.: WO03/043985

PCT Pub. Date: May 30, 2003

(65) Prior Publication Data

US 2004/0248936 A1    Dec. 9, 2004

Related U.S. Application Data

(60) Provisional application No. 60/396,906, filed on Jul. 18, 2002, provisional application No. 60/331,986, filed on Nov. 21, 2001.

(51) Int. Cl.
   *A61K 31/422*     (2006.01)
   *A61K 31/405*     (2006.01)
   *C07D 263/32*     (2006.01)
   *C07D 209/30*     (2006.01)

(52) U.S. Cl. ............ 514/374; 514/419; 548/235; 548/492

(58) Field of Classification Search .......... 548/235, 548/492; 514/374, 419
See application file for complete search history.

(56) References Cited

U.S. PATENT DOCUMENTS 5,036,153 A * 7/1991 Braish et al. ............. 548/542
5,254,543 A    10/1993 Hanko et al. ............. 514/89
5,795,890 A * 8/1998 Nakae et al. ............ 514/235.5

FOREIGN PATENT DOCUMENTS

| EP | 0 769 498 | 4/1997 |
|---|---|---|
| WO | WO 92/03423 | 3/1992 |
| WO | WO 99/00387 | 1/1999 |
| WO | WO 99/32466 | 7/1999 |
| WO | WO 00/35442 | 6/2000 |
| WO | WO 00/50418 | 8/2000 |
| WO | WO 00/64888 | 11/2000 |

OTHER PUBLICATIONS

Malamas et al., J. Med. Chem. No. 43, pp. 995-1010, New Azolidinediones as Inhibitors of Protein Tyrosine Phosphatase 1B with Antihyperglycemic Properties.

* cited by examiner

Primary Examiner—Joseph K. McKane
Assistant Examiner—Michael Barker
(74) Attorney, Agent, or Firm—Mark Milstead

(57) ABSTRACT

Compounds of the formula

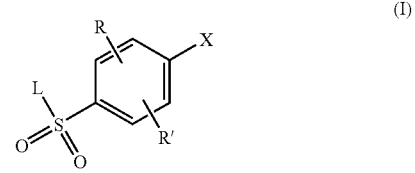

(I)

provide pharmacological agents which are potent agonists of Peroxisome Proliferator-Activated Receptors (PPARs). Accordingly, the compounds of the instant invention are useful for the treatment of conditions mediated by the PPAR receptor activity in mammals. Such conditions include dyslipidemia, hyperlipidemia, hypercholesteremia, atherosclerosis, hypertriglyceridemia, heart failure, myocardial infarction, vascular diseases, cardiovascular diseases, hypertension, obesity, inflammation, arthritis, cancer, Alzheimer's disease, skin disorders, respiratory diseases, ophthalmic disorders, inflammatory bowel diseases, ulcerative colitis and Crohn's disease. The compounds of the present invention are particularly useful in mammals as hypoglycemic agents for the treatment and prevention of conditions in which impaired glucose tolerance, hyperglycemia and insulin resistance are implicated, such as type-1 and type-2 diabetes, and Syndrome X. Preferred are the compounds of the invention which are dual agonists of PPARα and PPARγ receptors.

19 Claims, No Drawings

HETEROCYCLIC COMPOUNDS AND METHODS OF USE

The present invention relates to heterocyclic compounds, pharmaceutical compositions containing them and to methods of treating conditions associated with the Retinoid X Receptor (RXR) and the Peroxisome Proliferator-Activated Receptor (PPAR) families with the three subtypes PPARα, PPARδ and PPARγ.

In one aspect the present invention provides compounds of the formula

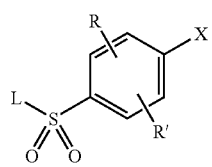

(I)

wherein
L is

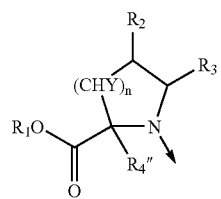

radical in which $R_1$ is hydrogen, optionally substituted alkyl, aryl, heteroaryl, aralkyl or cycloalkyl;
$R_2$ is hydrogen, hydroxy, optionally substituted alkyl, aryl, aralkyl, alkoxy, aryloxy, aralkoxy, alkylthio, arylthio or aralkylthio;
$R_3$ is hydrogen or aryl; or
$R_2$ and $R_3$ combined are alkylene which together with the carbon atoms they are attached to form a 5- to 7-membered ring;
n is zero or an integer from 1 to 2;
Y is hydrogen; or
Y and $R_2$ taken together with the carbon atoms they are attached to form a bond provided that n is 1;
$R_4$ is hydrogen; or
$R_4$ and Y taken together with the carbon atoms they are attached to form a bond provided that n is 1, and $R_2$ and $R_3$ taken together with the carbon atoms they are attached to form a bond; or
L is

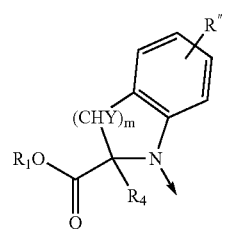

radical in which $R_1$ is hydrogen, optionally substituted alkyl, aryl, heteroaryl, aralkyl or cycloalkyl;
R" is hydrogen, optionally substituted alkyl, alkoxy or halogen;
m is an integer from 1 to 2;
Y is hydrogen;
$R_4$ is hydrogen; or
$R_4$ and Y taken together with the carbon atoms they are attached to form a bond provided that m is 1;
R and R' are independently hydrogen, halogen, optionally substituted alkyl, alkoxy, aralkyl or heteroaralkyl; or
R and R' combined together form a methylenedioxy group provided that R and R' are attached to carbon atoms adjacent to each other; or
R and R' combined together with the carbon atoms they are attached to form an optionally substituted 5- to 6-membered aromatic or heteroaromatic ring provided that R and R' are attached to carbon atoms adjacent to each other; or
R—C and R'—C may independently be replaced by nitrogen;
X is —Z—$(CH_2)_p$—Q—W wherein Z is a bond, O, S, S(O), S(O)$_2$, —C(O)— or —C(O)NR$_5$— in which
$R_5$ is hydrogen, alkyl or aralkyl;
p is an integer from 1 to 8;
Q is a bond provided that Z is not a bond when p is 1; or
Q is —O(CH$_2$)$_r$— or —S(CH$_2$)$_r$— in which r is zero or an integer from 1 to 8; or
Q is —O(CH$_2$)$_{1-8}$O—, —S(CH$_2$)$_{1-8}$O—, —S(CH$_2$)$_{1-8}$S—, —C(O)— or —C(O)NR$_6$— in which $R_6$ is hydrogen, optionally substituted alkyl, cycloalkyl, aryl, heteroaryl, aralkyl or heteroaralkyl; or
Q is —NR$_6$—, —NR$_5$C(O)—, —NR$_5$C(O)NH— or —NR$_5$C(O)O— provided that p is not 1;
W is cycloalkyl, aryl, heterocyclyl, aralkyl or heteroaralkyl; or
W and $R_6$ taken together with the nitrogen atom to which they are attached form a
8- to 12-membered bicyclic ring, which may be optionally substituted or may contain another heteroatom selected from oxygen, nitrogen and sulfur;

or a pharmaceutically acceptable salt thereof; or an optical isomer thereof; or a mixture of optical isomers thereof.

In another aspect the present invention provides methods of treating conditions mediated by the PPAR receptor activity in mammals. Such conditions include dyslipidemia, hyperlipidemia, hypercholesteremia, atherosclerosis, hypertriglyceridemia, heart failure, myocardial infarction, vascular diseases, cardiovascular diseases, hypertension, obesity, inflammation, arthritis, cancer, Alzheimer's disease, skin disorders, respiratory diseases, ophthalmic disorders, IBDs (irritable bowel disease), ulcerative colitis and Crohn's disease. The compounds of the present invention are particularly useful in mammals as hypoglycemic agents for the treatment and prevention of conditions in which impaired glucose tolerance, hyperglycemia and insulin resistance are implicated, such as type-1 and type-2 diabetes and Syndrome X. Preferred are the compounds of the invention which are dual agonists of PPARα and PPARγ receptors.

The present invention relates to heterocyclic compounds, pharmaceutical compositions containing them, methods for preparing the compounds and methods of treating conditions mediated by the RXR and the PPAR families, including activation of PPARs, using such compounds. The compounds of the invention may also be used in combination with ligands for other nuclear receptors which are known to form heterodimeric complexes with the RXR receptors.

Further, the present invention relates to pharmaceutical compositions containing the heterocyclic compounds of the invention for the treatment of the conditions mentioned hereinabove.

Listed below are definitions of various terms used to describe the compounds of the instant invention. These definitions apply to the terms as they are used throughout the specification and the claims unless they are otherwise limited in specific instances either individually or as part of a larger group, e.g., wherein an attachment point of a certain group is limited to a specific atom within that group, the point of attachment is defined by an arrow at the specific atom.

The term "optionally substituted alkyl" refers to unsubstituted or substituted straight or branched chain hydrocarbon groups having 1 to 20 carbon atoms, preferably 1 to 7 carbon atoms. Exemplary unsubstituted alkyl groups include methyl, ethyl, propyl, isopropyl, n-butyl, t-butyl, isobutyl, pentyl, hexyl, isohexyl, heptyl, 4,4-dimethylpentyl, octyl and the like. Substituted alkyl groups include, but are not limited to, alkyl groups substituted by one or more of the following groups: halo, hydroxy, cycloalkyl, alkanoyl, alkoxy, alkyloxyalkoxy, alkanoyloxy, amino, alkylamino, dialkylamino, alkanoylamino, thiol, alkylthio, alkylthiono, alkylsulfonyl, arylsulfonyl, heteroarylsulfonyl, sulfonamido, nitro, cyano, carboxy, alkoxycarbonyl, aryl, alkenyl, alkynyl, aralkoxy, guanidino, heterocyclyl including indolyl, imidazolyl, furyl, thienyl, thiazolyl, pyrrolidyl, pyridyl, pyrimidyl, piperidyl, morpholinyl and the like.

The term "lower alkyl" refers to those alkyl groups as described above having 1 to 7, preferably 1 to 4 carbon atoms.

The term "halogen" or "halo" refers to fluorine, chlorine, bromine and iodine.

The term "alkenyl" refers to any of the above alkyl groups having at least two carbon atoms and further containing a carbon to carbon double bond at the point of attachment. Groups having two to four carbon atoms are preferred.

The term "alkynyl" refers to any of the above alkyl groups having at least two carbon atoms and further containing a carbon to carbon triple bond at the point of attachment. Groups having two to four carbon atoms are preferred.

The term "alkylene" refers to a straight chain bridge of 1 to 6 carbon atoms connected by single bonds (e.g., —$(CH_2)_x$— wherein x is 1 to 6), which may be substituted with 1 to 3 lower alkyl or alkoxy groups.

The term "cycloalkyl" refers to optionally substituted monocyclic, bicyclic or tricyclic hydrocarbon groups of 3 to 12 carbon atoms, each of which may optionally be substituted by one or more substituents, such as alkyl, halo, oxo, hydroxy, alkoxy, alkanoyl, amino, alkylamino, dialkylamino, thiol, alkylthio, nitro, cyano, carboxy, carboxyalkyl, alkoxycarbonyl, alkyl- and arylsulfonyl, sulfonamido, heterocyclyl and the like.

Exemplary monocyclic hydrocarbon groups include, but are not limited to, cyclopropyl, cyclobutyl, cyclopentyl, cyclopentenyl, cyclohexyl and cyclohexenyl and the like.

Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like.

Exemplary tricyclic hydrocarbon groups include adamantyl and the like.

The term "alkoxy" refers to alkyl-O—.

The term "acyl" refers to alkanoyl, aroyl, heteroaroyl, arylalkanoyl or heteroarylalkanoyl.

The term "alkanoyl" refers to alkyl-C(O)—.

The term "alkanoyloxy" refers to alkyl-C(O)—O—.

The terms "alkylamino" and "dialkylamino" refer to alkyl-NH— and (alkyl)$_2$N—, respectively.

The term "alkanoylamino" refers to alkyl-C(O)—NH—.

The term "alkylthio" refers to alkyl-S—.

The term "alkylaminothiocarbonyl" refers to alkyl-NHC(S)—.

The term "trialkylsilyl" refers to (alkyl)$_3$Si—.

The term "trialkylsilyloxy" refers to (alkyl)$_3$SiO—.

The term "alkylthiono" refers to alkyl-S(O)—.

The term "alkylsulfonyl" refers to alkyl-S(O)$_2$—.

The term "alkoxycarbonyl" refers to alkyl-O—C(O)—.

The term "alkoxycarbonyloxy" refers to alkyl-O—C(O)O—.

The term "carbamoyl" refers to alkyl-NHC(O)—, (alkyl)$_2$NC(O)—, aryl-NHC(O)—, alkyl(aryl)-NC(O)—, heteroaryl-NHC(O)—, alkyl(heteroaryl)-NC(O)—, aralkyl-NHC(O)— and alkyl(aralkyl)-NC(O)—.

The term "aryl" refers to monocyclic or bicyclic aromatic hydrocarbon groups having 6 to 12 carbon atoms in the ring portion, such as phenyl, naphthyl, tetrahydronaphthyl, biphenyl and diphenyl groups, each of which may optionally be substituted by one to four substituents, such as alkyl, halo, hydroxy, alkoxy, alkanoyl, alkanoyloxy, optionally substituted amino, thiol, alkylthio, nitro, cyano, carboxy, carboxyalkyl, alkoxycarbonyl, alkylthiono, alkyl- and arylsulfonyl, sulfonamido, heterocycloyl and the like.

The term "monocyclic aryl" refers to optionally substituted phenyl as described under aryl.

The term "aralkyl" refers to an aryl group bonded directly through an alkyl group, such as benzyl.

The term "aralkylthio" refers to aralkyl-S—.

The term "aralkoxy" refers to an aryl group bonded directly through an alkoxy group.

The term "arylsulfonyl" refers to aryl-S(O)$_2$—.

The term "arylthio" refers to aryl-S—.

The term "aroyl" refers to aryl-C(O)—.

The term "aroylamino" refers to aryl-C(O)—NH—.

The term "aryloxycarbonyl" refers to aryl-O—C(O)—.

The term "heterocyclyl" or "heterocyclo" refers to an optionally substituted, fully saturated or unsaturated, aromatic or non-aromatic cyclic group, for example, which is a 4- to 7-membered monocyclic, 7- to 12-membered bicyclic, or 10- to 15-membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized. The heterocyclic group may be attached at a heteroatom or a carbon atom.

Exemplary monocyclic heterocyclic groups include pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like.

Exemplary bicyclic heterocyclic groups include indolyl, dihydroidolyl, benzothiazolyl, benzoxazinyl, benzoxazolyl, benzothienyl, benzothiazinyl, quinuclidinyl, quinolinyl, tetrahydroquinolinyl, decahydroquinolinyl, isoquinolinyl, tetrahydroisoquinolinyl, decahydroisoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]-pyridinyl] or furo[2,3-b]pyridinyl), dihydroisoindolyl, dihydroquinazolinyl (such as 3,4-dihydro-4-oxo-quinazolinyl), phthalazinyl and the like.

Exemplary tricyclic heterocyclic groups include carbazolyl, dibenzoazepinyl, dithienoazepinyl, benzindolyl, phenanthrolinyl, acridinyl, phenanthridinyl, phenoxazinyl, phenothiazinyl, xanthenyl, carbolinyl and the like.

The term "heterocyclyl" includes substituted heterocyclic groups. Substituted heterocyclic groups refer to heterocyclic groups substituted with 1, 2 or 3 of the following:
(a) alkyl;
(b) hydroxy (or protected hydroxy);
(c) halo;
(d) oxo (i.e.=O);
(e) optionally substituted amino, alkylamino or dialkylamino;
(f) alkoxy;
(g) cycloalkyl;
(h) carboxy;
(i) heterocyclooxy;
j) alkoxycarbonyl, such as unsubstituted lower alkoxycarbonyl;
(k) mercapto;
(l) nitro;
(m) cyano;
(n) sulfonamido, sulfonamidoalkyl, sulfonamidoaryl or sulfonamidodialkyl;
(O) aryl;
(p) alkylcarbonyloxy;
(q) arylcarbonyloxy;
(r) arylthio;
(s) aryloxy;
(t) alkylthio;
(u) formyl;
(v) carbamoyl;
(w) aralkyl; or
(x) aryl substituted with alkyl, cycloalkyl, alkoxy, hydroxy, amino, alkylamino, dialkylamino or halo.

The term "heterocyclooxy" denotes a heterocyclic group bonded through an oxygen bridge.

The term "heteroaryl" refers to an aromatic heterocycle, for example monocyclic or bicyclic aryl, such as pyrrolyl, pyrazolyl, imidazolyl, oxazolyl, isoxazolyl, thiazolyl, isothiazolyl, furyl, thienyl, pyridyl, pyrazinyl, pyrimidinyl, pyridazinyl, indolyl, benzothiazolyl, benzoxazolyl, benzothienyl, quinolinyl, isoquinolinyl, benzimidazolyl, benzofuryl and the like; optionally substituted by, e.g., lower alkyl, lower alkoxy or halo.

The term "heteroarylsulfonyl" refers to heteroaryl-$S(O)_2$—.

The term "heteroaroyl" refers to heteroaryl-$C(O)$—.

The term "heteroaralkyl" refer to a heteroaryl group bonded through an alkyl group.

Encompassed by the invention are prodrug derivatives, e.g., any pharmaceutically acceptable prodrug ester derivatives of the carboxylic acids of the invention which are convertible by solvolysis or under physiological conditions to the free carboxylic acids.

Examples of such carboxylic acid esters are preferably lower alkyl esters, cycloalkyl esters, lower alkenyl esters, benzyl esters, mono or disubstituted lower alkyl esters, e.g., the ω-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxy-methyl ester, and the like conventionally used in the art.

The compounds of the invention depending on the nature of the substituents, may possess one or more asymmetric centers. The resulting diastereoisomers, optical isomers, i.e., enantiomers, and geometric isomers are encompassed by the instant invention.

Preferred are compounds of the formula I wherein
X is —Z—$(CH_2)_P$—Q—W wherein Z is a bond, O, S, —C(O)— or —C(O)$NR_5$— in which
$R_5$ is hydrogen, alkyl or aralkyl;
p is an integer from 1 to 8;
Q is a bond provided that Z is not a bond when p is 1; or
Q is —O$(CH_2)_r$— or —S$(CH_2)_r$— in which r is zero or an integer from 1 to 8; or
Q is —O$(CH_2)_{1-8}$O—, —S$(CH_2)_{1-8}$O—, —S$(CH_2)_{1-8}$S—, —C(O)— or —C(O)$NR_6$— in which $R_6$ is hydrogen, optionally substituted alkyl, cycloalkyl, aryl, heteroaryl, aralkyl or heteroaralkyl; or
Q is —$NR_6$—, —$NR_5C(O)$—, —$NR_5C(O)NH$— or —$NR_5C(O)O$— provided that p is not 1;
W is cycloalkyl, aryl, heterocyclyl, aralkyl or heteroaralkyl; or
W and $R_6$ taken together with the nitrogen atom to which they are attached form a 8- to 12-membered bicyclic ring, which may be optionally substituted or may contain another heteroatom selected from oxygen, nitrogen and sulfur;

or a pharmaceutically acceptable salt thereof; or an optical isomer thereof; or a mixture of optical isomers thereof.

Further preferred are compounds of the formula

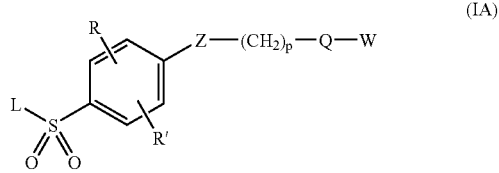

(IA)

wherein
L is

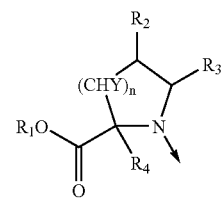

radical in which $R_1$ is hydrogen or optionally substituted alkyl;
$R_2$ and $R_3$ are hydrogen; or
$R_2$ and $R_3$ combined are alkylene which together with the carbon atoms they are attached to form a 6-membered ring;
n is zero or an integer from 1 to 2;
Y is hydrogen;
$R_4$ is hydrogen; or L is

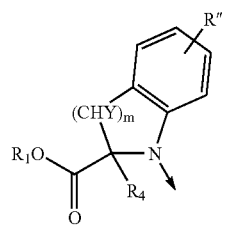

radical in which $R_1$ is hydrogen or optionally substituted alkyl;

R" is hydrogen, optionally substituted alkyl, alkoxy or halogen;

m is an integer from 1 to 2;

Y is hydrogen;

$R_4$ is hydrogen;

R and R' are independently hydrogen, halogen, optionally substituted $C_{1-6}$alkyl or $C_{1-6}$alkoxy; or R and R' combined together form a methylenedioxy group provided that R and R' are attached to carbon atoms adjacent to each other;

Z is a bond, O, S or —C(O)NR$_5$— in which $R_5$ is hydrogen, alkyl or aralkyl;

p is an integer from 1 to 5;

Q is a bond provided that Z is not a bond when p is 1; or

Q is —O(CH$_2$)$_r$— or —S(CH$_2$)$_r$— in which r is zero; or

Q is —C(O)— or —C(O)NR$_5$— in which $R_6$ is hydrogen, optionally substituted alkyl, cycloalkyl, aryl, heteroaryl, aralkyl or heteroaralkyl; or Q is —NR$_6$—, —NR$_5$C(O)—, —NR$_5$C(O)NH— or —NR$_5$C(O)O— provided that p is not 1;

W is cycloalkyl, aryl or heterocyclyl; or W and $R_6$ taken together with the nitrogen atom to which they are attached form a 9- to 10-membered bicyclic ring, which may be optionally substituted or may contain another heteroatom selected from oxygen, nitrogen and sulfur;

or a pharmaceutically acceptable salt thereof; or an optical isomer thereof; or a mixture of optical isomers thereof.

More preferred are the compounds of the formula IA wherein

L is

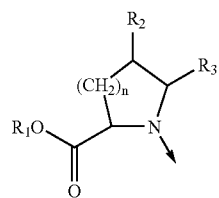

radical in which $R_1$ is hydrogen or optionally substituted alkyl;

$R_2$ and $R_3$ are hydrogen;

n is zero or an integer from 1 to 2; or

L is

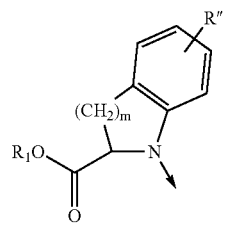

radical in which $R_1$ is hydrogen or optionally substituted alkyl;

R" is hydrogen;

m is an integer from 1 to 2;

R is hydrogen, halogen, optionally substituted $C_{1-6}$alkyl or $C_{1-6}$alkoxy;

R' is hydrogen;

Z is a bond, O or S;

p is an integer from 1 to 5;

Q is a bond provided that Z is not a bond when p is 1; or

Q is O, S or —C(O)NR$_6$— in which $R_6$ is hydrogen, optionally substituted alkyl or cycloalkyl; or Q is —NR$_6$—, —NR$_5$C(O)NH— or —NR$_5$C(O)O— in which $R_5$ is hydrogen, alkyl or aralkyl provided that p is not 1;

W is cycloalkyl, aryl or heterocyclyl; or W and $R_6$ taken together with the nitrogen atom to which they are attached form a 9- to 10-membered bicyclic ring, which may be optionally substituted or may contain another heteroatom selected from oxygen, nitrogen and sulfur;

or a pharmaceutically acceptable salt thereof; or an optical isomer thereof; or a mixture of optical isomers thereof.

Most preferred are the compounds of the formula (IB)

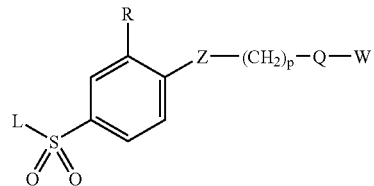

wherein

L is

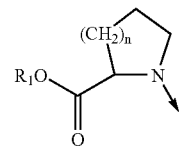

radical in which $R_1$ is hydrogen or optionally substituted alkyl;

n is zero or 1; or

L is

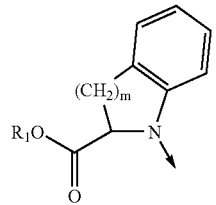

radical in which $R_1$ is hydrogen or optionally substituted alkyl;

m is 1;

R is hydrogen, halogen, optionally substituted $C_{1-6}$alkyl or $C_{1-6}$alkoxy;

Z is a bond, O or S;

p is an integer from 1 to 5;

Q is a bond provided that Z is not a bond when p is 1; or

Q is O, S or —C(O)$NR_6$— in which $R_6$ is hydrogen, optionally substituted alkyl or cycloalkyl; or Q is —$NR_6$—, —$NR_5$C(O)NH— or —$NR_5$C(O)O— in which $R_5$ is hydrogen, alkyl or aralkyl provided that p is not 1;

W is cycloalkyl, aryl or heterocyclyl; or W and $R_6$ taken together with the nitrogen atom to which they are attached form a 9- to 10-membered bicyclic ring, which may be optionally substituted or may contain another heteroatom selected from oxygen, nitrogen and sulfur;

or a pharmaceutically acceptable salt thereof; or an optical isomer thereof; or a mixture of optical isomers thereof.

Further preferred are compounds of formula IB wherein

L is

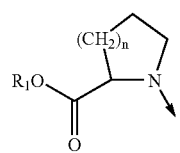

radical in which $R_1$ is hydrogen; and n is zero or 1;

R is hydrogen, halogen, optionally substituted $C_{1-6}$alkyl or $C_{1-6}$alkoxy;

Z is a bond, O or S;

p is an integer from 1 to 4;

Q is a bond provided that Z is not a bond when p is 1; or

Q is O or S;

W is aryl or heterocyclyl;

or a pharmaceutically acceptable salt thereof; or an optical isomer thereof; or a mixture of optical isomers thereof.

Further preferred are also the compounds of formula IB wherein

L is

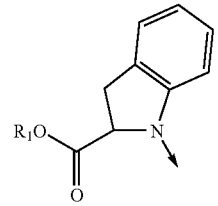

radical in which $R_1$ is hydrogen;

R is hydrogen, halogen, optionally substituted $C_{1-6}$alkyl or $C_{1-6}$alkoxy;

Z is a bond, O or S;

p is an integer from 1 to 4;

Q is a bond provided that Z is not a bond when p is 1; or

Q is O or S;

W is aryl or heterocyclyl;

or a pharmaceutically acceptable salt thereof; or an optical isomer thereof; or a mixture of optical isomers thereof.

Further preferred are also the compounds of formula IB wherein the asymmetric center in radical L is in the (R) configuration; or a pharmaceutically acceptable salt thereof.

Further preferred are also the compounds of formula IB, designated as the A group, wherein $R_1$ is hydrogen or optionally substituted alkyl;

R is hydrogen, halogen, optionally substituted $C_{1-6}$alkyl or $C_{1-6}$alkoxy;

Z is O or S;

p is 2;

Q is a —$NR_5$— in which $R_6$ is lower alkyl;

W is aryl or heterocyclyl;

or a pharmaceutically acceptable salt thereof; or an optical isomer thereof; or a mixture of optical isomers thereof.

Preferred are the compounds in the A group wherein

R is hydrogen, chloro, n-propyl or methoxy;

or a pharmaceutically acceptable salt thereof; or an optical isomer thereof; or a mixture of optical isomers thereof.

Further preferred are also the compounds of formula IB, designated as the B group, wherein $R_1$ is hydrogen or optionally substituted alkyl;

R is hydrogen, halogen, optionally substituted $C_{1-6}$alkyl or $C_{1-6}$alkoxy;

Z is a bond;

p is 2;

Q is a —C(O)$NR_6$— in which $R_6$ is optionally substituted alkyl;

W is aryl or heterocyclyl; or

W and $R_6$ taken together with the nitrogen atom to which they are attached form a 9- to 10-membered bicyclic ring, which may be optionally substituted or may contain another heteroatom selected from oxygen, nitrogen and sulfur;

or a pharmaceutically acceptable salt thereof; or an optical isomer thereof; or a mixture of optical isomers thereof.

Preferred are the compounds in the B group wherein

R is hydrogen, chloro, n-propyl or methoxy;

or a pharmaceutically acceptable salt thereof; or an optical isomer thereof; or a mixture of optical isomers thereof.

Further preferred are also the compounds of formula IB, designated as the C group, wherein $R_1$ is hydrogen or optionally substituted alkyl;

R is hydrogen, halogen, optionally substituted $C_{1-6}$alkyl or $C_{1-6}$alkoxy;

Z is a bond, O or S;

p is an integer from 2 to 3;

Q is O or S;

W is aryl or heterocyclyl;

or a pharmaceutically acceptable salt thereof; or an optical isomer thereof; or a mixture of optical isomers thereof.

Preferred are the compounds in the C group wherein

R is hydrogen, chloro, n-propyl or methoxy;

or a pharmaceutically acceptable salt thereof; or an optical isomer thereof; or a mixture of optical isomers thereof.

Another preferred group of compounds in the C group are the compounds wherein

W is selected from the group consisting of:

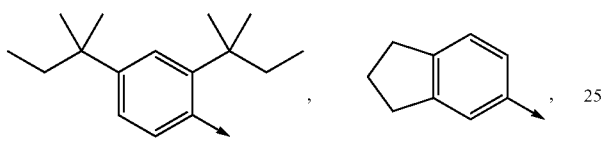,

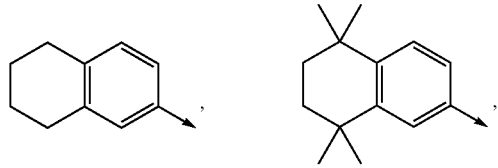,

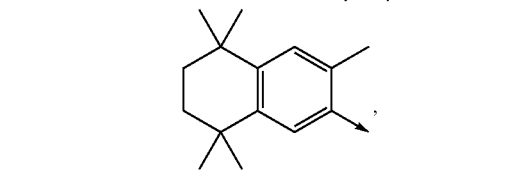,

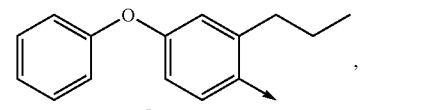,

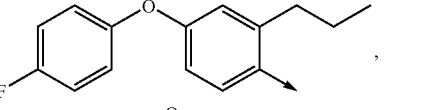,

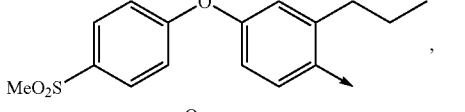,

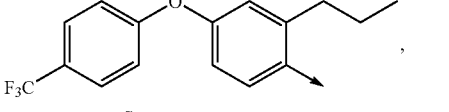,

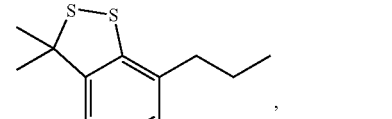,

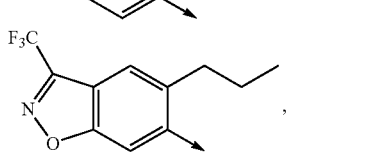,

-continued

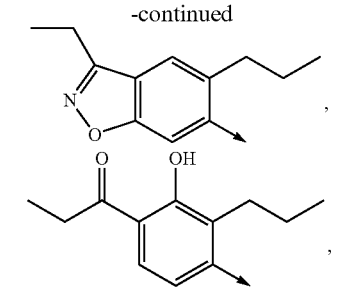,

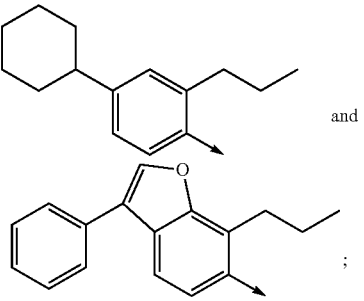, and

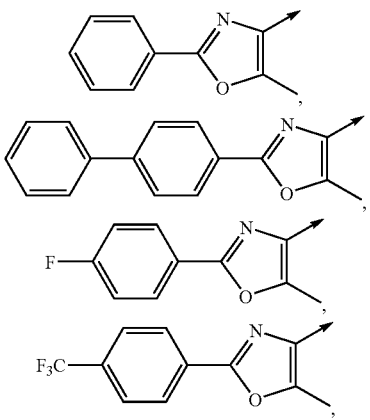;

or a pharmaceutically acceptable salt thereof; or an optical isomer thereof; or a mixture of optical isomers thereof.

Further preferred are also the compounds of formula IB, designated as the D group, wherein $R_1$ is hydrogen or optionally substituted alkyl;

R is hydrogen, halogen, optionally substituted $C_{1-6}$alkyl or $C_{1-6}$alkoxy;

Z is O or S;

p is an integer from 1 to 2;

Q is a bond;

W is aryl or heterocyclyl;

or a pharmaceutically acceptable salt thereof; or an optical isomer or a mixture of optical isomers thereof.

Preferred are the compounds in the D group wherein

R is hydrogen, chloro, n-propyl or methoxy;

or a pharmaceutically acceptable salt thereof; or an optical isomer thereof; or a mixture of optical isomers thereof.

Another preferred group of compounds in the D group are the compounds wherein

W is selected from the group consisting of:

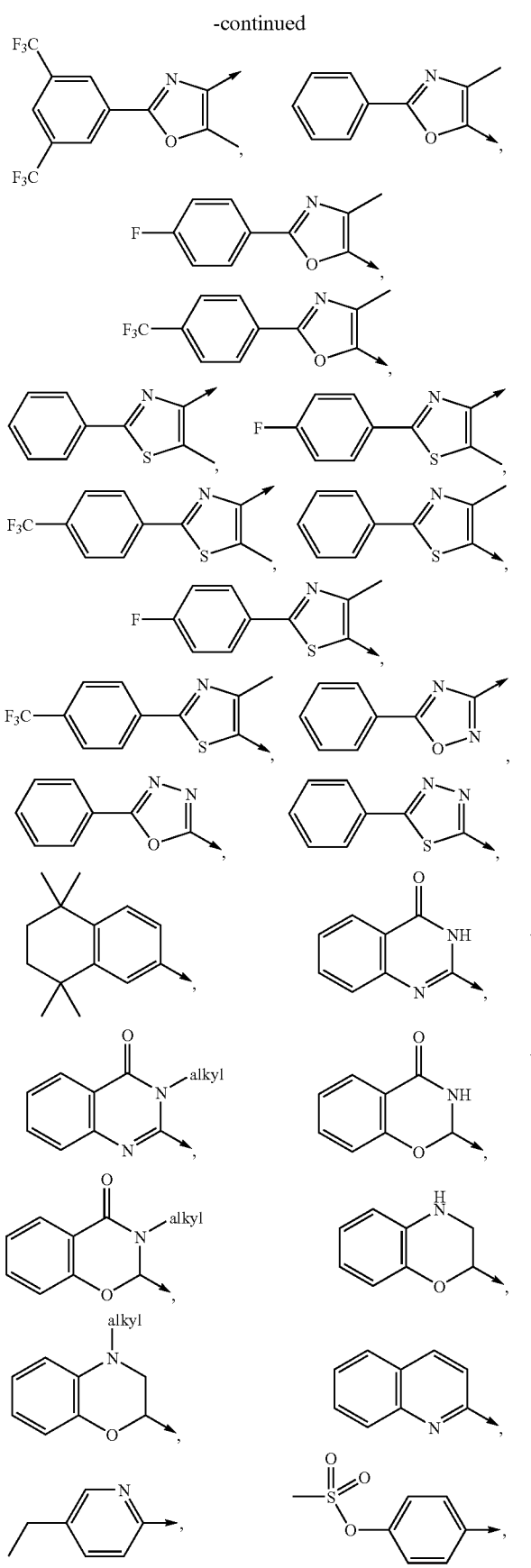

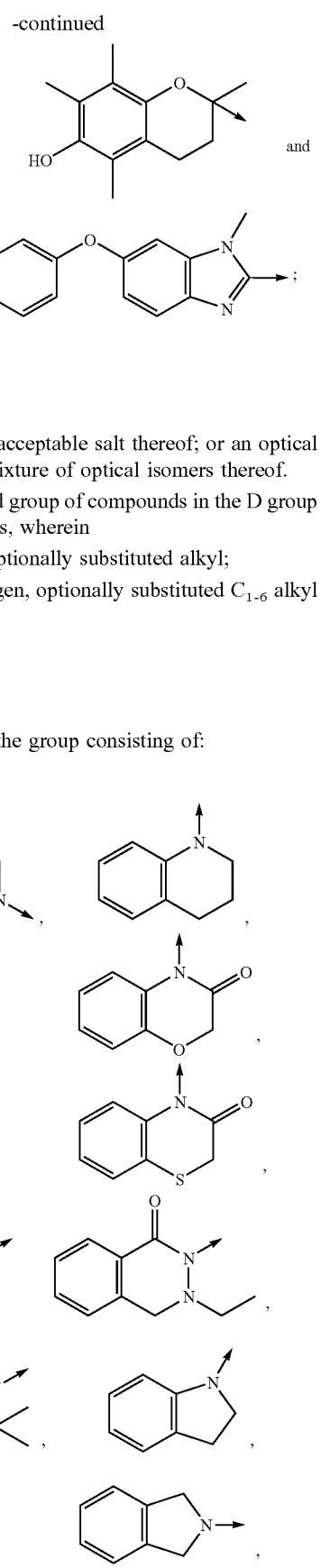

or a pharmaceutically acceptable salt thereof; or an optical isomer thereof; or a mixture of optical isomers thereof.

Yet another preferred group of compounds in the D group are also the compounds, wherein $R_1$ is hydrogen or optionally substituted alkyl;

R is hydrogen, halogen, optionally substituted $C_{1-6}$ alkyl or $C_{1-8}$ alkoxy;

Z is O or S;

p is 2;

Q is a bond;

W is selected from the group consisting of:

-continued

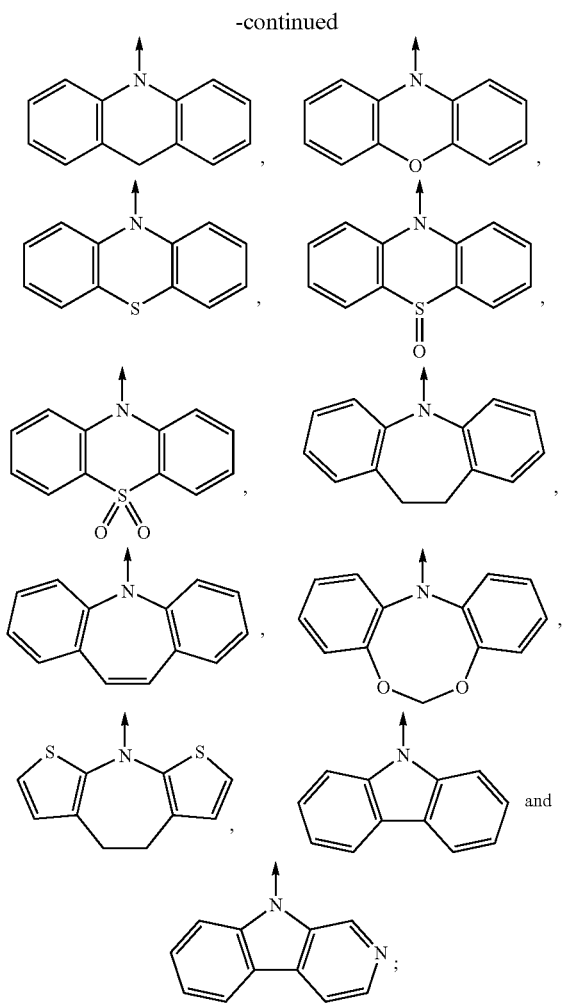

or a pharmaceutically acceptable salt thereof; or an optical isomer thereof; or a mixture of optical isomers thereof.

Particular embodiments of the invention are:

(R)-1-{4-[4-(4-Phenoxy-2-propyl-phenoxy)-butoxy]-benzenesulfonyl}-azetidine-2-carboxylic acid;

(R)-1-{4-[3-(4-Phenoxy-2-propyl-phenoxy)-propoxy]-benzenesulfonyl}-azetidine-2-carboxylic acid;

(R)-1-[4-(5-Methyl-2-phenyl-oxazol-4-ylmethoxy)-benzenesulfonyl]-azetidine-2-carboxylic acid;

(R)-1-{4-[2-(4-Fluoro-phenyl)-5-methyl-oxazol-4-ylmethoxy]-benzenesulfonyl}-azetidine-2-carboxylic acid;

(R)-1-{4-[5-Methyl-2-(4-trifluoromethyl-phenyl)-oxazol-4-ylmethoxy]-benzenesulfonyl}-azetidine-2-carboxylic acid;

(R)-1-{4-[2-(3,5-Bis-trifluoromethyl-phenyl)-5-methyl-oxazol-4-ylmethoxy]-benzene-sulfonyl}-azetidine-2-carboxylic acid;

(R)-1-{4-[2-(5-Methyl-2-phenyl-oxazol-4-yl)-ethoxy]-benzenesulfonyl}-azetidine-2-carboxylic acid;

(R)-1-{4-[4-(4-Phenoxy-2-propyl-phenoxy)-butoxy]-benzenesulfonyl}-pyrrolidine-2-carboxylic acid;

(R)-1-{4-[3-(4-Phenoxy-2-propyl-phenoxy)-propoxy]-benzenesulfonyl}-pyrrolidine-2-carboxylic acid;

(R)-1-(4-{3-[2-Propyl-4-(4-trifluoromethyl-phenoxy)-phenoxy]-propoxy}-benzenesulfonyl)-pyrrolidine-2-carboxylic acid;

(R)-1-{4-[2-(4-Phenoxy-2-propyl-phenoxy)-ethoxy]-benzenesulfonyl}-pyrrolidine-2-carboxylic acid;

(R)-1-(4-{2-[2-Propyl-4-(4-trifluoromethyl-phenoxy)-phenoxy]-ethoxy}-benzenesulfonyl)-pyrrolidine-2-carboxylic acid;

(R)-1-{3-Methoxy-4-[3-(4-phenoxy-2-propyl-phenoxy)-propoxy]-benzenesulfonyl}-pyrrolidine-2-carboxylic acid;

(R)-1-{3-Chloro-4-[3-(4-phenoxy-2-propyl-phenoxy)-propoxy]-benzenesulfonyl}-pyrrolidine-2-carboxylic acid;

(R)-1-{4-[3-(4-Phenoxy-2-propyl-phenoxy)-propoxy]-3-propyl-benzenesulfonyl}-pyrrolidine-2-carboxylic acid;

(R)-1-{4-[3-(4-Phenoxy-2-propyl-phenoxy)-propylsulfanyl]-benzenesulfonyl}-pyrrolidine-2-carboxylic acid;

(R)-1-{4-[2-(4-Phenoxy-2-propyl-phenoxy)-ethylsulfanyl]-benzenesulfonyl}-pyrrolidine-2-carboxylic acid;

(R)-1-{4-[3-(4-Phenoxy-2-propyl-phenoxy)-propyl]-benzenesulfonyl}-pyrrolidine-2-carboxylic acid;

(R)-1-[4-(5-Methyl-2-phenyl-oxazol-4-ylmethoxy)-benzenesulfonyl]-pyrrolidine-2-carboxylic acid;

(R)-1-{4-[2-(4-Fluoro-phenyl)-5-methyl-oxazol-4-ylmethoxy]-benzenesulfonyl}-pyrrolidine-2-carboxylic acid;

(R)-1-{4-[5-Methyl-2-(4-trifluoromethyl-phenyl)-oxazol-4-ylmethoxy]-benzenesulfonyl}-pyrrolidine-2-carboxylic acid;

(R)-1-{4-[2-(3,5-Bis-trifluoromethyl-phenyl)-5-methyl-oxazol-4-ylmethoxy]-benzene-sulfonyl}-pyrrolidine-2-carboxylic acid;

(R)-1-[4-(2-Biphenyl-4-yl-5-methyl-oxazol-4-ylmethoxy)-benzenesulfonyl]-pyrrolidine-2-carboxylic acid;

(R)-1-[3-Methoxy-4-(5-methyl-2-phenyl-oxazol-4-ylmethoxy)-benzenesulfonyl]-pyrrolidine-2-carboxylic acid;

(R)-1-[3-Chloro-4-(5-methyl-2-phenyl-oxazol-4-ylmethoxy)-benzenesulfonyl]-pyrrolidine-2-carboxylic acid;

(R)-1-[4-(5-Methyl-2-phenyl-oxazol-4-ylmethoxy)-3-propyl-benzenesulfonyl]-pyrrolidine-2-carboxylic acid;

(R)-1-[4-(5-Methyl-2-phenyl-oxazol-4-ylmethylsulfanyl)-benzenesulfonyl]-pyrrolidine-2-carboxylic acid;

(R)-1-{4-[2-(4-Fluoro-phenyl)-5-methyl-oxazol-4-ylmethylsulfanyl]-benzenesulfonyl}-pyrrolidine-2-carboxylic acid;

(R)-1-{4-[5-Methyl-2-(4-trifluoromethyl-phenyl)-oxazol-4-ylmethylsulfanyl]-benzenesulfonyl}-pyrrolidine-2-carboxylic acid;

(R)-1-{4-[2-(3,5-Bis-trifluoromethyl-phenyl)-5-methyl-oxazol-4-ylmethylsulfanyl]-benzenesulfonyl}-pyrrolidine-2-carboxylic acid;

(R)-1-{4-[2-(5-Methyl-2-phenyl-oxazol-4-yl)-ethoxy]-benzenesulfonyl}-pyrrolidine-2-carboxylic acid;

(R)-1-{3-Methoxy-4-[2-(5-methyl-2-phenyl-oxazol-4-yl)-ethoxy]-benzenesulfonyl}-pyrrolidine-2-carboxylic acid;

(R)-1-{3-Chloro-4-[2-(5-methyl-2-phenyl-oxazol-4-yl)-ethoxy]-benzenesulfonyl}-pyrrolidine-2-carboxylic acid;

(R)-1-(4-{2-[5-Methyl-2-(4-trifluoromethyl-phenyl)-oxazol-4-yl]-ethoxy}-benzenesulfonyl)-pyrrolidine-2-carboxylic acid;

(R)-1-{4-[2-(5-Methyl-2-phenyl-oxazol-4-yl)-ethylsulfanyl]-benzenesulfonyl}-pyrrolidine-2-carboxylic acid;

(R)-1-{4-[4-(4-Phenoxy-2-propyl-phenoxy)-butoxy]-benzenesulfonyl}-2,3-dihydro-1H-indole-2-carboxylic acid;

(R)-1-{4-[3-(4-Phenoxy-2-propyl-phenoxy)-propoxy]-benzenesulfonyl}-2,3-dihydro-1H-indole-2-carboxylic acid;

(R)-1-{4-[2-(4-Phenoxy-2-propyl-phenoxy)-ethoxy]-benzenesulfonyl}-2,3-dihydro-1H-indole-2-carboxylic acid;

(R)-1-{3-Methoxy-4-[3-(4-phenoxy-2-propyl-phenoxy)-propoxy]-benzenesulfonyl}-2,3-dihydro-1H-indole-2-carboxylic acid;

(R)-1-{3-Chloro-4-[3-(4-phenoxy-2-propyl-phenoxy)-propoxy]-benzenesulfonyl}-2,3-dihydro-1H-indole-2-carboxylic acid;

(R)-1-{4-(5-Methyl-2-phenyl-oxazol-4-ylmethoxy)-benzenesulfonyl}-2,3-dihydro-1H-indole-2-carboxylic acid;

(R)-1-{4-[2-(4-Fluoro-phenyl)-5-methyl-oxazol-4-ylmethoxy]-benzenesulfonyl}-2,3-dihydro-1H-indole-2-carboxylic acid;

(R)-1-{4-[5-Methyl-2-(4-trifluoromethyl-phenyl)-oxazol-4-ylmethoxy]-benzenesulfonyl}-2,3-dihydro-1H-indole-2-carboxylic acid;

(R)-1-{4-[2-(3,5-Bis-trifluoromethyl-phenyl)-5-methyl-oxazol-4-ylmethoxy]-benzene-sulfonyl}-2,3-dihydro-1H-indole-2-carboxylic acid;

(R)-1-[3-Methoxy-4-(5-methyl-2-phenyl-oxazol-4-ylmethoxy)-benzenesulfonyl]-2,3-dihydro-1H-indole-2-carboxylic acid;

(R)-1-[3-Chloro-4-(5-methyl-2-phenyl-oxazol-4-ylmethoxy)-benzenesulfonyl-2,3-dihydro-1H-indole-2-carboxylic acid;

(R)-1-[4-(5-Methyl-2-phenyl-oxazol-4-ylmethoxy)-3-propyl-benzenesulfonyl]-2,3-dihydro-1H-indole-2-carboxylic acid;

(R)-1-[4-(5-Methyl-2-phenyl-oxazol-4-ylmethylsulfanyl)-benzenesulfonyl]-2,3-dihydro-1H-indole-2-carboxylic acid;

(R)-1-{4-[2-(4-Fluoro-phenyl)-5-methyl-oxazol-4-ylmethylsulfanyl]-benzenesulfonyl}-2,3-dihydro-1H-indole-2-carboxylic acid;

(R)-1-{4-[5-Methyl-2-(4-trifluoromethyl-phenyl)-oxazol-4-ylmethylsulfanyl]-benzenesulfonyl}-2,3-dihydro-1H-indole-2-carboxylic acid;

(R)-1-{4-[2-(3,5-Bis-trifluoromethyl-phenyl)-5-methyl-oxazol-4-ylmethylsulfanyl]-benzenesulfonyl}-2,3-dihydro-1H-indole-2-carboxylic acid;

(R)-1-{4-[2-(5-Methyl-2-phenyl-oxazol-4-yl)-ethoxy]-benzenesulfonyl}-2,3-dihydro-1H-indole-2-carboxylic acid;

(R)-1-{3-Chloro-4-[2-(5-methyl-2-phenyl-oxazol-4-yl)-ethoxy]-benzenesulfonyl}-2,3-dihydro-1H-indole-2-carboxylic acid;

(R)-1-{4-[5-Methyl-2-(4-trifluoromethyl-phenyl)-oxazol-4-ylmethylsulfanyl]-benzene-sulfonyl}-pyrrolidine-2-carboxylic acid; and (R)-1-{4-[5-Methyl-2-(4-trifluoromethyl-phenyl)-oxazol-4-ylmethylsulfanyl]-benzene-sulfonyl}-2,3-dihydro-1H-indole-2-carboxylic acid;

or a pharmaceutically acceptable salt thereof; or an enantiomer thereof; or a mixture of enantiomers thereof.

Pharmaceutically acceptable salts of any acidic compounds of the invention are salts formed with bases, namely cationic salts such as alkali and alkaline earth metal salts, such as sodium, lithium, potassium, calcium, magnesium, as well as ammonium salts, such as ammonium, trimethylammonium, diethylammonium, and tris-(hydroxymethyl)-methyl-ammonium salts.

Similarly acid addition salts, such as of mineral acids, organic carboxylic and organic sulfonic acids, e.g., hydrochloric acid, methanesulfonic acid, maleic acid, are possible provided a basic group, such as pyridyl, constitutes part of the structure.

Compounds of formula I may be prepared starting from sulfonic acid analogs of the formula

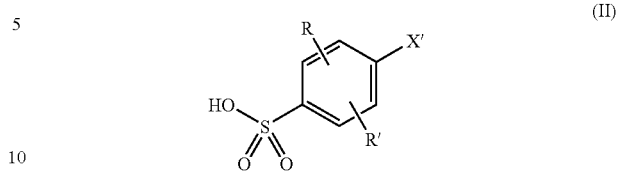

in which R and R' have meanings as defined herein, X' represents X as defined herein, or X' is a group convertible to X. Compounds of formula II may be first treated with a chlorinating agent, such as thionyl chloride or oxalyl chloride to form sulfonyl chlorides of the formula

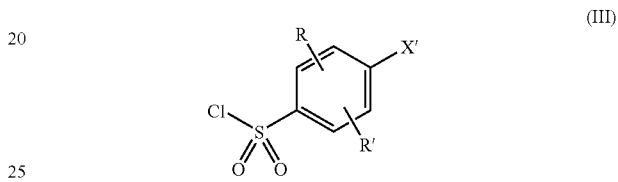

wherein R, R' and X' have meanings as defined herein above, using reaction conditions described herein, or using conditions well-known in the art.

Sulfonyl chlorides of formula III wherein R, R' and X' have meanings as defined herein above can then be reacted with amines of the formula

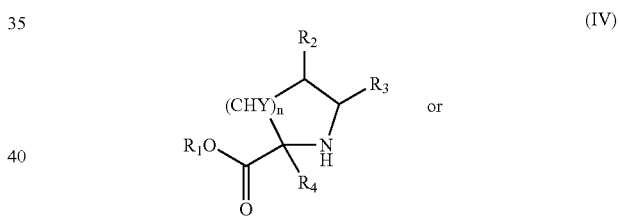

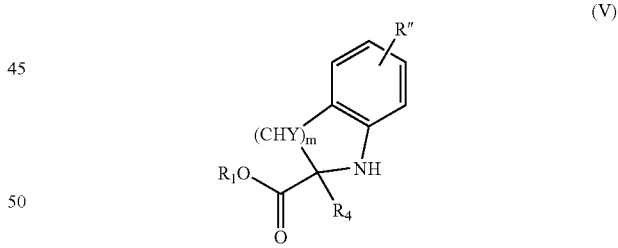

in which $R_1$, $R_2$, $R_3$, $R_4$, n, Y, R" and m have meanings as defined herein, in the presence of a base, such as triethylamine, diisopropylethylamine or N-methylmorpholine in an inert solvent, such as dichloromethane, N,N-dimethylformamide or tetrahydrofuran to obtain compounds of the formula

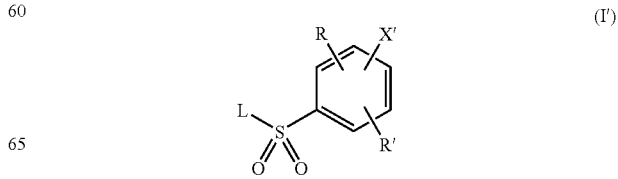

wherein R, R' and X' have meanings as defined herein above and L represents

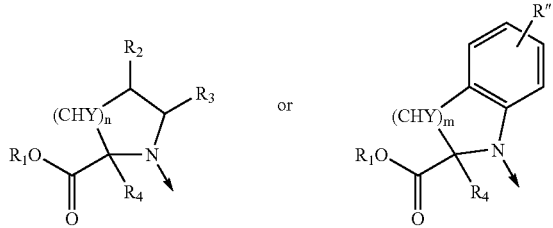

radical wherein $R_1$, $R_2$, $R_3$, $R_4$, n, Y, R" and m have meanings as defined herein above. Amines of formula IV and V may be obtained by methods described herein or modifications thereof, or by methods known in the art.

Compounds of formula I' wherein X' represents X as defined herein can be obtained from compounds of formula I' wherein X' is a group convertible to X using methods described herein or modifications thereof, or using methods well known in the art. For example, compounds of formula I' in which X' is benzyloxy can be first converted to compounds of the formula

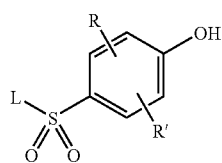

wherein R, R' and L have meanings as defined herein above, e.g., by reduction with hydrogen in the presence of a catalyst, such as palladium on carbon in a polar organic solvent, such as ethyl acetate or ethanol. The resulting phenols of the formula VI may then be treated with an alkylating agent of the formula

wherein p, Q and W have meanings as defined herein and Lg represents a leaving group such as bromide, chloride or trifluoromethanesulfonate, in the presence of a base, such as potassium carbonate or sodium hydride in an inert solvent, such as N,N-dimethylformamide or tetrahydrofuran to form compounds of formula I' in which X' is —O—$(CH_2)_p$—O—W and p, Q and W have meanings as defined herein.

Alternatively, compounds of formula I' wherein X' is —O—$(CH_2)_p$—Q—W, and p, Q and W have meanings as defined herein may be obtained from sulfonic acid analogs of formula II in which X' is hydroxy, and R and R' have meanings as defined herein, by converting a compound of formula II to its dialkali metal salt, e.g., a disodium salt, using aqueous base, e.g., aqueous sodium hydroxide, in a polar solvent, such as 1,4-dioxane, followed by treatment with an alkylating agent of formula VII wherein p, Q and W have meanings as defined herein and Lg represents a leaving group, such as bromide, chloride or trifluoro-methane-sulfonate to form compounds of the formula

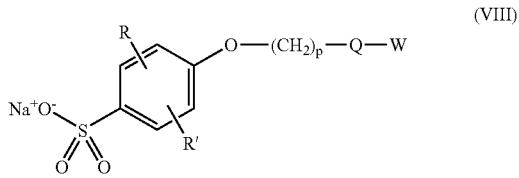

wherein R, R', p, 0 and W have meaning as defined herein.

Compounds of formula VIII wherein R, R', p, Q and W have meaning as defined herein may be treated with a chlorinating agent, such as thionyl chloride or oxalyl chloride to afford sulfonyl chlorides of the formula

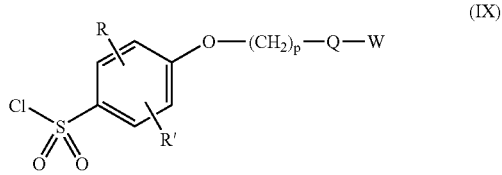

wherein R, R', p, Q and W have meaning as defined herein. Sulfonyl chlorides of formula IX can be reacted with amines of formulae IV or V, or acid addition salts thereof, in which $R_1$ is hydrogen, and $R_2$, $R_3$, n, Y, R" and m have meanings as defined herein, in the presence of a base such as aqueous sodium hydroxide in a polar solvent, such as 1,4-dioxane to form compounds of formula I' in which X' is —O—$(CH_2)_p$—Q—W and p, Q and W have meanings defined herein.

Similarly, compounds of formula I' wherein R, R' and L have meanings as defined herein above, and X' is thiol can be converted to compounds of formula I' in which X' is —S—$(CH_2)_p$—Q—W. For example, thiols of the formula

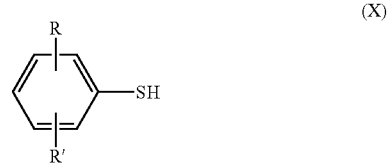

wherein R and R' have meanings as defined herein may be dimerized by methods well known in the art to form disulfides of the formula

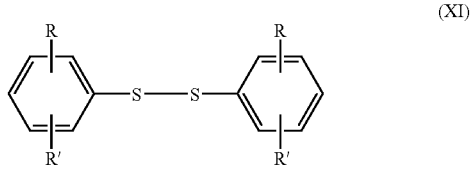

wherein R and R' have meanings as defined herein.

Compounds of formula XI wherein R and R' have meanings as defined herein can be converted to bis sulfonylchloride analogs of the formula

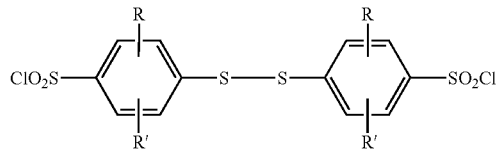

(XII)

wherein R and R' have meanings as defined herein, by treatment with chlorosulfonic acid in an inert solvent, such as dichloromethane followed by basic hydrolysis using, e.g., aqueous sodium hydroxide. The resulting bis sodium salts can then be treated with a chlorinating agent, such as thionyl chloride or oxalyl chloride to form sulfonyl chlorides of formula XII.

Sulfonyl chlorides of formula XII wherein R and R' have meanings as defined herein may be reacted with amines of the formula

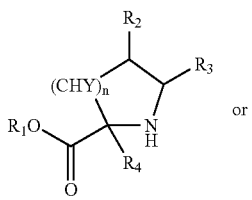

or

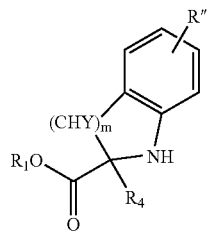

(IV)

(V)

in which $R_1$, $R_2$, $R_3$, $R_4$, n, Y, R" and m have meanings as defined herein, in the presence of a base, such as triethylamine, diisopropylethylamine or N-methylmorpholine in an inert solvent, such as dichloromethane, N,N-dimethylformamide or tetrahydrofuran to afford disulfides of the formula

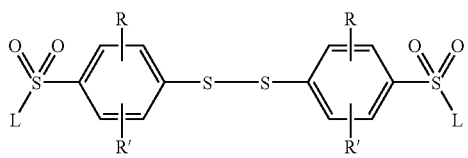

(XIII)

wherein R and R' have meanings as defined herein above and L represents

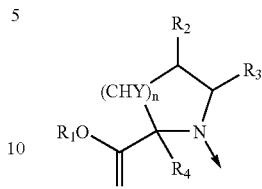 or 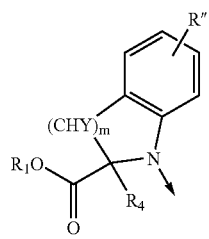

radical wherein $R_1$, $R_2$, $R_3$, $R_4$, n, Y, R" and m have meanings as defined herein above.

Disulfides of formula XIII wherein R, R' and L have meanings as defined herein can be reduced to thiols of the formula

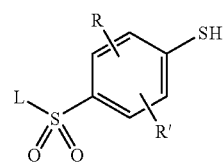

(XIV)

wherein R, R' and L have meanings as defined herein above, by treatment with a reducing agent, such as sodium borohydride or triphenylphosphine in a polar solvent, such as ethanol or tetrahydrofuran, respectively.

Thiols of formula XIV may then be treated with an alkylating agent of the formula Lg—(CH$_2$)$_p$—Q—W          (VII)

wherein p, Q and W have meanings as defined herein and Lg represents a leaving group, such as bromide, chloride or trifluoromethanesulfonate, in the presence of a base, such as potassium carbonate or sodium hydride in an inert solvent, such as N,N-dimethylformamide or tetrahydrofuran to form compounds of formula I' in which X' is —S—(CH$_2$)$_p$—Q—W, and p, Q and W have meanings defined herein.

Preferably, the alkylating agent of formula VII is selected from a group wherein p is an integer from 2 to 5, Q is O, Lg is chloride or bromide and W is

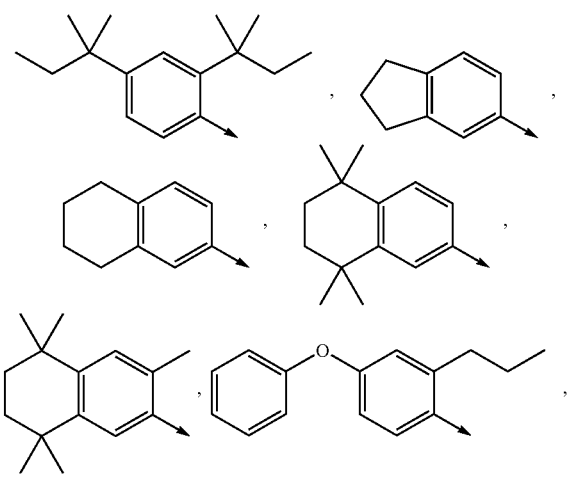

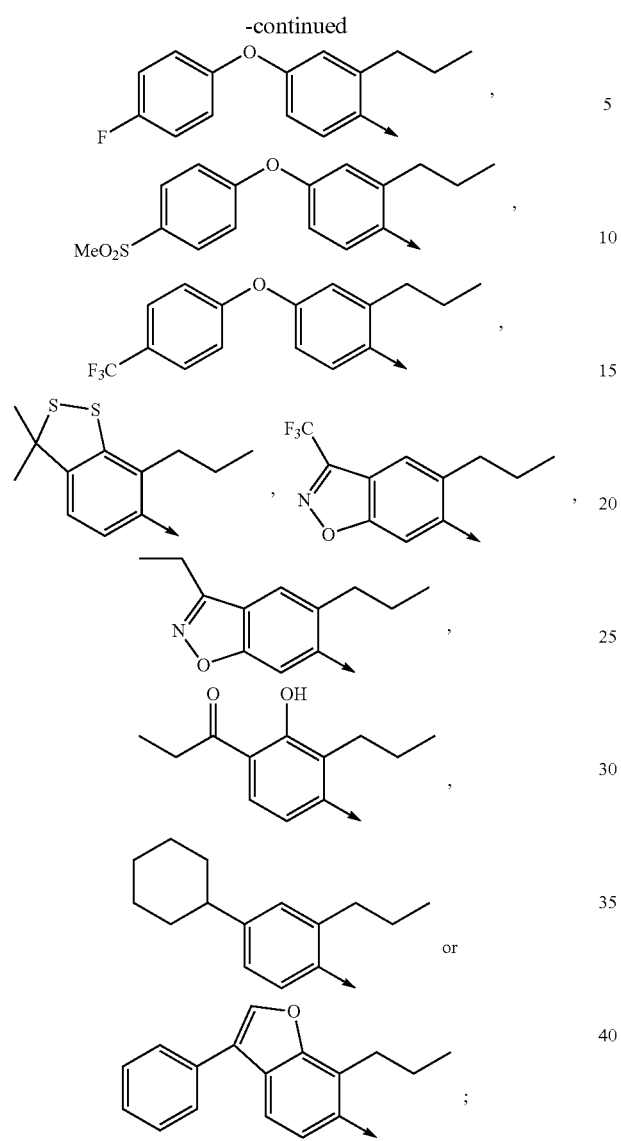
or the alkylating agent of formula VII is selected from a group wherein p is 1 to 2, Q is a bond, Lg chloride or bromide and W is
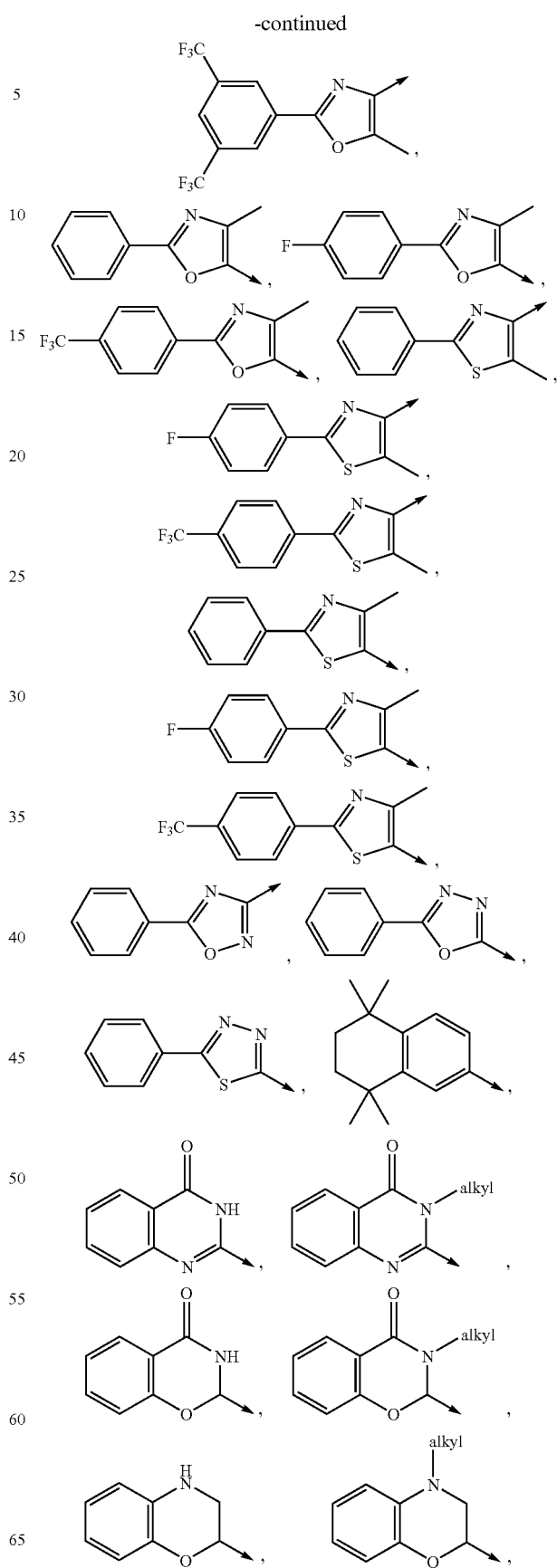

-continued

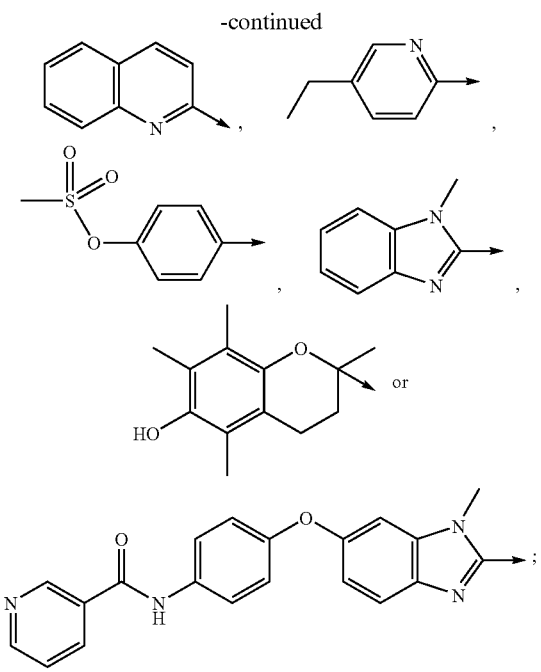

or the alkylating agent of formula VII is selected from a group wherein p is 2, Q is a bond, Lg chloride or bromide and W is

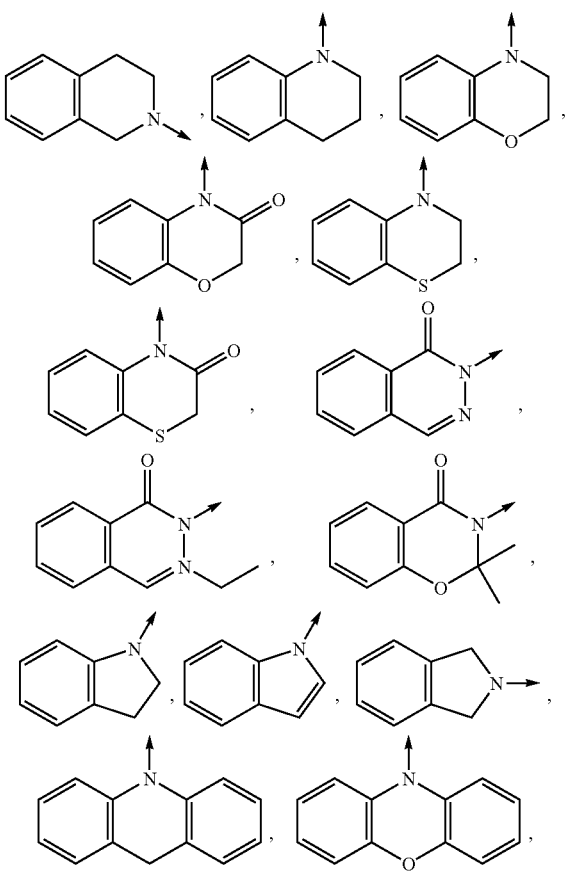

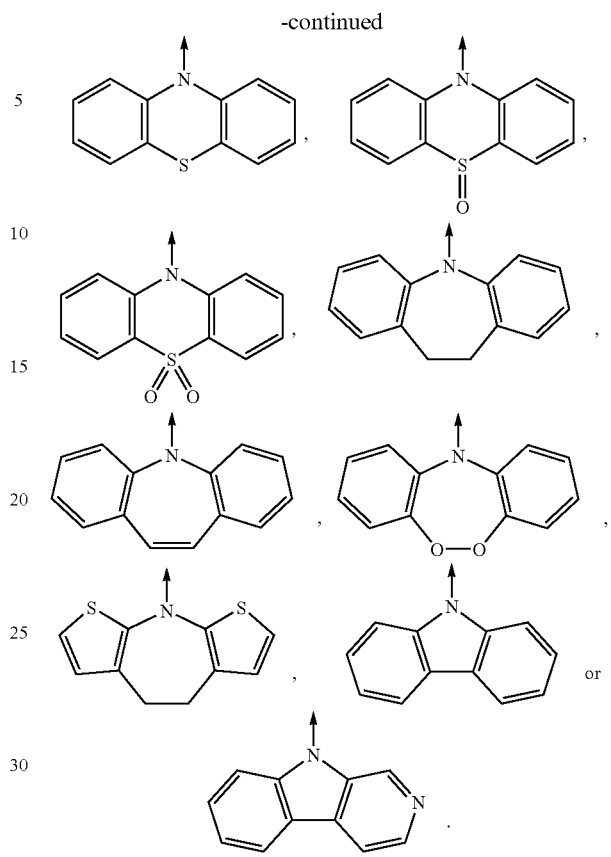

The alkylating agents of formula VII may be prepared using methods described herein or modifications thereof, or using methods known in the art, e.g., 4-chloromethyl-5-methyl-2-phenyloxazole and 4-chloromethyl-5-methyl-2-[4-(trifluoromethyl)-phenyl]-oxazole may be prepared using methods described in International PCT Patent Application No. WO 00/64888 or according to *J. Med. Chem.*, Vol. 43, pp. 995–1010 (2000). 1-(3-Bromopropoxy)-4-phenoxy-2-propyl-benzene may be prepared as described in International PCT Patent Application No. WO 00/78312.

Preferably, alkylating agents of formula VII having the formula

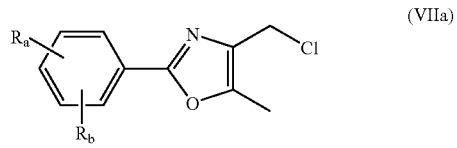

(VIIa)

wherein $R_a$ and $R_b$ are independently hydrogen, halogen, alkyl, alkoxy, trifluoromethyl or aryl, may be prepared by treating a compound of the formula

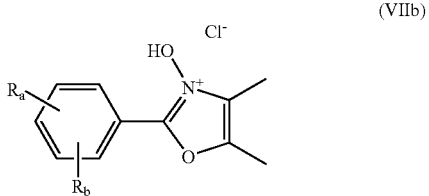

(VIIb)

wherein $R_a$ and $R_b$ have meanings as defined for formula VIIa, with a chlorinating agent, such as phosphorus oxychloride ($POCl_3$), in acetonitrile. It is essential that the reaction is carried out in acetonitrile in order to obtain alkylating agents of formula VIIIa in high chemical yield and purity, i.e., the alkylating agents of formula VIIa are obtained according to the present method in high regioselectivity, preferably in greater than 99% selectivity. The chlorination is preferably conducted at an ambient temperature, e.g. at room temperature.

Compounds of formula VIIb may be prepared by condensing an aldehyde of the formula

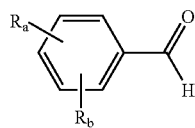

(VIIc)

wherein $R_a$ and $R_b$ have meanings as defined for formula VIIIb, with 2,3-butadione monooxime of the formula

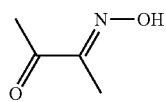

(VIId)

in the presence of an acid catalyst, such as gaseous hydrochloric acid and an organic solvent, such as ethyl acetate or acetic acid, preferably glacial acetic acid, to afford compounds of formula VIIb wherein $R_a$ and $R_b$ have meanings as defined herein above.

In a preferred embodiment, the alkylating agent of formula VIIIa is 4-chloromethyl-5-methyl-2-[4-(trifluoromethyl)phenyl]-oxazole.

Alternatively, phenols of formula VI and thiols of formula XIV may also be reacted with alcohols of the formula

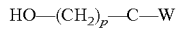

$HO-(CH_2)_p-C-W$ (VII')

wherein p, Q and W have meanings defined herein, under Mitsunobu conditions, e.g., in the presence of triphenylphoshine and diethyl azodicarboxylate in an organic solvent, such as tetrahydrofuran, to afford compounds of formula I' in which X' is $-O-(CH_2)_p-Q-W$ or $-S-(CH_2)_p-Q-W$, respectively, and p, Q and W have meanings as defined herein. Alcohols of formula VII" may be prepared by methods described herein or modifications thereof, or by methods well-known in the art.

Compounds of formula I' wherein X' is $-(CH_2)_p-Q-W$, and p and W have meanings as defined herein and Q represents O or S, may be obtained by reacting compounds of the formula

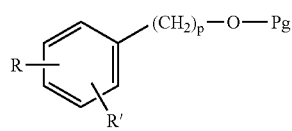

(XV)

wherein R, R' and p have meanings as defined herein above, and Pg represents a protecting group, such as acyl, e.g., acetyl or lower alkoxycarbonyl, with chlorosulfonic acid in an inert solvent, such as dichloromethane followed by subsequent treatment with a chlorinating agent, such as thionyl chloride or oxalyl chloride to afford sulfonyl chlorides of the formula

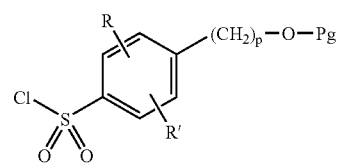

(XVI)

wherein R, R', p and Pg have meanings as defined herein above.

Sulfonyl chlorides of formula XVI may be coupled with amines of formula VI or V as described herein above to form compounds of the formula

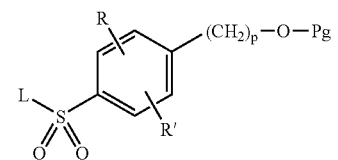

(XVII)

wherein R, R', p, Pg and L have meaning as defined herein. Subsequent removal of the protecting group using base, e.g., aqueous sodium hydroxide in a polar solvent, such as methanol, tetrahydrofuran or 1,4-dioxane, in particular when Pg is acetyl, affords alcohols of the formula

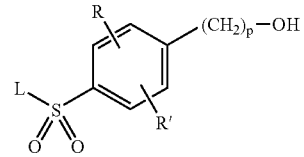

(XVIII)

wherein R, R', p and L have meanings as defined herein.

Alcohols of formula XVIII may be coupled with phenols of formula W—OH or thiols of formula W—SH, e.g., under Mitsunobu conditions, to form compounds of formula I' wherein R, R' and L have meanings as defined herein, and X' represents $-(CH_2)_p-Q-W$, in which p and W have meanings as defined herein, and Q is O or S, respectively.

Alternatively, alcohols of formula XVIII may be converted to compounds of the formula

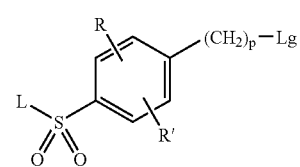

(XIX)

wherein R, R', p and L have meanings as defined herein and Lg represents a leaving group, such as chloride, bromide or trifluorosulfonate, using methods described herein or modifications thereof, or using methods well-known in the art. Subsequent reaction with phenols of formula W—OH or thiols of formula W—SH in the presence of a base, such as potassium carbonate; or sodium hydride in an inert solvent, such as N,N-dimethylformamide or tetrahydrofuran affords compounds of formula I' wherein R, R' and L have meanings as defined herein, and X' represents —(CH$_2$)$_p$—Q—W, in which p and W have meanings as defined herein, and Q is O or S, respectively.

Compounds of formula I' wherein R, R' and L have meanings as defined herein, and X' represents —C(O)NR$_5$—(CH$_2$)$_p$—Q—W, and R$_5$, p, Q and W have meanings defined herein, may be prepared by reacting an activated derivative of a carboxylic acid of the formula

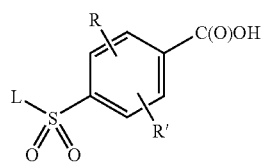

(XX)

wherein R, R' and L have meanings as defined herein and R$_1$ is optionally substituted alkyl, aryl, heteroaryl, aralkyl or cycloalkyl, with amines or acid addition salts thereof of the formula R$_5$—NH—(CH$_2$)$_p$—Q—W  (XXI)

wherein R$_5$, p, Q and W have meanings as defined herein. Carboxylic acids of formula XX and amines of formula XXI may be prepared using methods described herein or modifications thereof, or using methods known in the art.

Similarly, compounds of formula I' wherein R, R' and L have meanings as defined herein, and X' represents —Z—(CH$_2$)$_p$—C(O)NR$_6$—W, and Z, p, R$_6$ and W have meanings as defined herein, may be prepared by reacting an activated derivative of a carboxylic acid of the formula

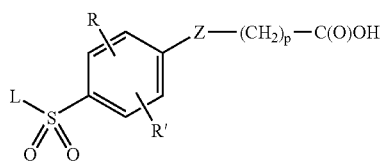

(XXII)

wherein R, R', L, Z and p have meanings as defined herein and R$_1$ is optionally substituted alkyl, aryl, heteroaryl, aralkyl or cycloalkyl, with amines or acid addition salts thereof of the formula

R$_6$—NH—W  (XXIII)

wherein R$_6$ and W have meanings as defined herein. Carboxylic acids of formula XXII and amines of formula XXIII may be prepared using methods described herein or modifications thereof, or using methods known in the art.

In the processes cited herein, activated derivatives of carboxylic acids, e.g., those of formulae XX and XXII, include acid chlorides, bromides and fluorides, mixed anhydrides, lower alkyl esters and activated esters thereof, and adducts formed with coupling agents, such as 1-ethyl-3-(3-dimethylaminopropyl)carbodiimide hydrochloride, O-(1,2-dihydro-2-oxo-1-pyridyl)-N,N,N',N'-tetramethyluronium tetrafluoroborate and the like. Mixed anhydrides are preferably such from pivalic acid, or lower alkyl hemiesters of carbonic acids, such as ethyl or isobutyl analogs. Activated esters include, for example, succinimido, phthalimido or 4-nitrophenyl esters. The reaction of an activated derivative of a carboxylic acid, e.g., those of formulae XX or XXII, with an amine, e.g., those of formulae XXI or XXIII, respectively, may be carried out in the presence of a base, such as triethylamine, diisopropylethylamine or N-methylmorpholine in an inert solvent, such as dichloromethane, N,N-dimethylformamide or tetrahydrofuran. Carboxylic acids of formulae XX and XXII can be converted to their activated derivatives using methods described herein or in the art.

Compounds of formula I' wherein R, R' and L have meanings as defined herein, and X' represents —Z—(CH$_2$)$_p$—NR$_5$C(O)—W, —Z—(CH$_2$)$_p$—NR$_5$C(O)NH—W or —Z—(CH$_2$)$_p$—NR$_5$C(O)O—W, and Z, p, R$_5$ and W have meanings as defined herein, may be obtained by reacting amines of the formula

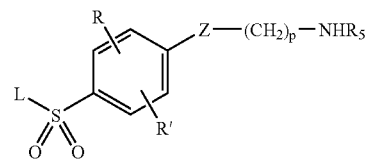

(XXIV)

wherein R, R', Z, p, R$_5$ and L have meanings as defined herein, and R$_1$ is optionally substituted alkyl, aryl, heteroaryl, aralkyl or cycloalkyl, with a N-derivatizing agent, such as an activated carboxylic acid derivative, an isocyanate or a chloroformate, respectively, in the presence of a base, such as triethylamine, diisopropylethylamine or N-methylmorpholine in an inert solvent, such as dichloromethane, N,N-dimethylformamide or tetrahydrofuran. Amines of formula XXIV may be prepared using methods described herein or modifications thereof, or using methods known in the art.

Compounds of formula I' in which R, R', L and X' have meanings as defined herein, and R$_1$ is optionally substituted alkyl, aryl, heteroaryl, aralkyl or cycloalkyl can be converted to compounds of the formula I' in which R$_1$ is hydrogen using reaction conditions described herein or modifications thereof, or using methods know in the art, e.g., compounds of formula I' in which R$_1$ is lower alkyl, such as methyl or ethyl; may be treated with an aqueous base, such as sodium or potassium hydroxide; in a polar solvent, such as methanol, ethanol, 1,4-dioxane or tetrahydrofuran to afford compounds of formula I' in which R, R', L and X' have meanings as defined herein, and R$_1$ is hydrogen.

The starting compounds and intermediates which are converted to the compounds of the invention in a manner described herein, functional groups present, such as amino, thiol, carboxyl and hydroxy groups, are optionally protected by conventional protecting groups that are common in preparative organic chemistry. Protected amino, thiol, carboxyl and hydroxy groups are those that can be converted under mild conditions into free amino, thiol, carboxyl and hydroxy groups without the molecular framework being destroyed or other undesired side reactions taking place.

The purpose of introducing protecting groups is to protect the functional groups from undesired reactions with reaction components under the conditions used for carrying out a desired chemical transformation. The need and choice of protecting groups for a particular reaction is known to those skilled in the art and depends on the nature of the functional group to be protected (hydroxy group, amino group, etc.), the structure and stability of the molecule of which the substituent is a part and the reaction conditions.

Well-known protecting groups that meet these conditions and their introduction and removal are described, e.g., in McOmie, "Protective Groups in Organic Chemistry", Plenum Press, London, N.Y. (1973); and Greene and Wuts, "Protective Groups in Organic Synthesis", John Wiley and Sons, Inc., NY (1999).

The above-mentioned reactions are carried out according to standard methods, in the presence or absence of diluent, preferably such as are inert to the reagents and are solvents thereof, or catalysts, condensing of said other agents respectively and/or inert atmospheres, at low temperatures, room temperature or elevated temperatures (preferably at or near the boiling point of the solvents used), and at atmospheric or super-atmospheric pressure. The preferred solvents, catalysts and reaction conditions are set forth in the appended illustrative Examples.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure antipodes.

Compounds of the invention and intermediates can also be converted into each other according to methods generally known per se.

The invention also relates to any novel starting materials and processes for their manufacture.

Depending on the choice of starting materials and methods, the compounds may be in the form of one of the possible isomers or mixtures thereof, for example, as substantially pure geometric (cis or trans) isomers, optical isomers (antipodes), racemates or mixtures thereof. The aforesaid possible isomers or mixtures thereof are within the purview of this invention.

Any resulting mixtures of isomers can be separated on the basis of the physico-chemical differences of the constituents, into the pure geometric or optical isomers, diastereoisomers, racemates, for example, by chromatography and/or fractional crystallization.

Any resulting racemates of final products or intermediates can be resolved into the optical antipodes by known methods, e.g., by separation of the diastereoisomeric salts thereof, obtained with an optically active acid or base, and liberating the optically active acidic or basic compound. The carboxylic acid intermediates can thus be resolved into their optical antipodes, e.g., by fractional crystallization of D- or L-(alpha-methylbenzylamine, cinchonidine, cinchonine, quinine, quinidine, ephedrine, dehydroabietylamine, brucine or strychnine)-salts. Racemic products can also be resolved by chiral chromatography, e.g., high pressure liquid chromatography using a chiral adsorbent.

Finally, compounds of the invention are either obtained in the free form, or as a salt thereof if salt forming groups are present.

Acidic compounds of the invention may be converted into salts with pharmaceutically acceptable bases, e.g., an aqueous alkali metal hydroxide, advantageously in the presence of an ethereal or alcoholic solvent, such as a lower alkanol. From the solutions of the latter, the salts may be precipitated with ethers, e.g., diethyl ether. Resulting salts may be converted into the free compounds by treatment with acids. These or other salts can also be used for purification of the compounds obtained.

Compounds of the invention having basic groups can be converted into acid addition salts, especially pharmaceutically acceptable salts. These are formed, for example, with inorganic acids, such as mineral acids, for example, sulfuric acid, a phosphoric or hydrohalic acid; or with organic carboxylic acids, such as ($C_1$–$C_4$)-alkanecarboxylic acids which, for example, are unsubstituted or substituted by halogen, for example, acetic acid, such as saturated or unsaturated dicarboxylic acids, for example, oxalic, succinic, maleic or fumaric acid, such as hydroxy-carboxylic acids, for example, glycolic, lactic, malic, tartaric or citric acid, such as amino acids, for example, aspartic or glutamic acid; or with organic sulfonic acids, such as ($C_1$–$C_4$)-alkylsulfonic acids, for example, methanesulfonic acid; or arylsulfonic acids which are unsubstituted or substituted, for example, by halogen. Preferred are salts formed with hydrochloric acid, methanesulfonic acid and maleic acid.

In view of the close relationship between the free compounds and the compounds in the form of their salts, whenever a compound is referred to in this context, a corresponding salt is also intended, provided such is possible or appropriate under the circumstances.

The compounds, including their salts, can also be obtained in the form of their hydrates, or include other solvents used for their crystallization.

The pharmaceutical compositions according to the invention are those suitable for enteral, such as oral or rectal; transdermal and parenteral administration to mammals, including man, for the treatment of conditions mediated by PPAR receptors, in particular, PPARα and PPARγ. Such conditions include those conditions mentioned hereinafter with respect to the treatment for which the compounds of the instant invention may be employed. The said pharmaceutical compositions comprise an effective amount of a pharmacologically active compound of the instant invention, alone or in combination with one or more pharmaceutically acceptable carriers.

The pharmacologically active compounds of the invention may be employed in the manufacture of pharmaceutical compositions comprising an effective amount thereof in conjunction or admixture with excipients or carriers suitable for either enteral or parenteral application. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1–75%, preferably about 1–50%, of the active ingredient.

Suitable formulations for transdermal application include a therapeutically effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

The pharmaceutical formulations contain a therapeutically effective amount of a compound of the invention as defined above, either alone or in a combination with another therapeutic agent, e.g., each at an effective therapeutic dose as reported in the art. Such therapeutic agents include insulin, insulin derivatives and mimetics; insulin secretagogues such as the sulfonylureas, e.g., Glipizide and Amaryl; insulinotropic sulfonylurea receptor ligands, such as meglitinides, e.g., nateglinide and repaglinide; insulin sensitizers, such as protein tyrosine phosphatase-1B (PTP-1B) inhibitors, GSK3 (glycogen synthase kinase-3) inhibitors or RXR ligands; biguanides, such as metformin; alpha-glucosidase inhibitors, such as acarbose; GLP-1 (glucagon like peptide-1), GLP-1 analogs, such as Exendin-4, and GLP-1 mimetics; DPPIV (dipeptidyl peptidase IV) inhibitors, e.g. isoleucin-thiazolidide; DPP728 and LAF237, hypolipidemic agents, such as 3-hydroxy-3-methyl-glutaryl coenzyme A (HMG-CoA) reductase inhibitors, e.g., lovastatin, pitavastatin, simvastatin, pravastatin, cerivastatin, mevastatin, velostatin, fluvastatin, dalvastatin, atorvastatin, rosuvastatin, fluindostatin and rivastatin, squalene synthase inhibitors or FXR (liver X receptor) and LXR (farnesoid X receptor) ligands, cholestyramine, fibrates, nicotinic acid and aspirin. A compound of the present invention may be administered either simultaneously, before or after the other active ingredient, either separately by the same or different route of administration or together in the same pharmaceutical formulation.

A unit dosage for a mammal of about 50–70 kg may contain between about 1 mg and 1000 mg, advantageously between about 5–500 mg of the active ingredient. The therapeutically effective dosage of active compound is dependent on the species of warm-blooded animal (mammal), the body weight, age and individual condition, on the form of administration, and on the compound involved.

The compounds of the present invention bind to PPAR receptors, and thus may be employed for the treatment of conditions mediated by the PPARs, in particular, PPARα and PPARγ. Such compounds may therefore be employed for the treatment of dyslipidemia, hyperlipidemia, hypercholesteremia, atherosclerosis, hypertriglyceridemia, heart failure, myocardial infarction, vascular diseases, cardiovascular diseases, hypertension, obesity, inflammation, arthritis, cancer, Alzheimer's disease, skin disorders, respiratory diseases, ophthalmic disorders, IBDs (irritable bowel disease), ulcerative colitis and Crohn's disease. In particular, the compounds of the present invention may be employed in mammals as hypoglycemic agents for the treatment and prevention of conditions in which impaired glucose tolerance, hyperglycemia and insulin resistance are implicated, such as type-1 and type-2 diabetes, and Syndrome X.

The above-cited properties are demonstrable in vitro and in vivo tests, using advantageously mammals, e.g., mice, rats, dogs, monkeys or isolated organs, tissues and preparations thereof. Said compounds can be applied in vitro in the form of solutions, e.g., preferably aqueous solutions, and in vivo either enterally, parenterally, advantageously intravenously, e.g., as a suspension or in aqueous solution. The dosage in vitro may range between about $10^{-5}$ molar and $10^{-10}$ molar concentrations. A therapeutically effective amount in vivo may range depending on the route of administration, between about 1 and 500 mg/kg, preferably between about 5 and 100 mg/kg.

The compounds of the invention bind to the PPARα and PPARγ receptors and thus may be employed as dual agonists of the PPARα and the PPARγ receptors in mammals.

The activity of a compound according to the invention can be assessed by the following methods or methods well-described in the art:

The in vitro functional binding to the PPARα, PPARδ and PPARγ receptors is determined as follows:

The functional binding assays for the PPARα, PPARδ and PPARγ receptors are a variation of the coactivator-dependent receptor ligand assay (CARLA) (see Krey et al., "Fatty Acids, Eicosanoids, and Hypolipidemic Agents Identified as Ligands of Peroxisome Proliferator-Activated Receptors by Coactivator-Dependent Receptor Ligand Assay", *Molecular Endocrinology*, Vol. 11, pp. 779–791 (1997)). The present CARLA assays use a TR-FRET detection method previously reviewed (see Hemmila, "LANCE: Homogeneous Assay Platform for HTS", *J. Biomol. Screening*, Vol. 4, pp. 303–307 (1999); Mathis, "HTRF Technology", *J. Biomol. Screening*, Vol. 4, pp. 309–313 (1999)). All assays included 3 nM of the glutathione-S-transferase (GST) fusion proteins of either the hPPARα ligand binding domain (LBD) (amino acids 167–468) (GST-hPPARα LBD), GST-hPPARδ LBD (amino acids 139–442) or GST-hPPARγ LBD (amino acids 175–476); 3 nM Eu-labeled anti-GST antibody (Wallac); 30 nM biotinylated steroid receptor coactivator-1 (SRC-1) peptide (an N-terminal biotinylated peptide, CPSSHSSLTER-HKILHRLLQEGSPS, derived from amino acids 676–700 of SRC-1); and 10 nM streptavidin-labelled allophycocyanin (APC; Prozyme). The binding of a ligand to a PPAR LBD alters the conformation of the LBD and permits the biotinylated SRC-1 peptide to bind. This brings the Eu-labeled anti-GST antibody and the strepavidin-labeled APC in close proximity, thereby facilitating fluorescence energy transfer. The biotinylated SRC-1 peptide is prepared by standard solid-phase peptide synthetic methods. The GST-PPAR LBDs are expressed in pGEX vectors (Amersham Pharmacia) in the *E. coli* strain BL21 (DE3) using standard expression conditions at 18° C. In some cases the GST-PPAR LBDs are co-expressed with groESL. The GST fusion proteins are purified on glutathione sepharose affinity columns (Amersham Pharmacia) using the method described by the manufacturer. The assay buffer contained 50 mM Tris pH 7.4, 50 mM KCl, 0.1% BSA and 1 mM DTT (dithiothreitol). The assay is carried out in black half area 96-well plates in a final volume of 25 μL. After mixing all components, the reaction mixture stands for 3 hours at room temperature before reading the TR-FRET (Time-Resolved Fluorescence Resonance Energy Transfer) signal on a Wallac Victor 2 plate reader (measuring the ratio of signals at 665 nM and 620 nM). $EC_{50}$ values are estimated with the Excel add-in program XLFit (ID Business Solutions, Guildford, Surrey, UK) utilizing a 4-parameter logistic equation.

The glucose and insulin lowering activity in vivo can be evaluated as follows:

Adult male C57BL ob/ob mice (Jackson Lab, Bar Harbor, Me.) at the age of 11 weeks are housed six per cage in a reversed light cycle room (light on from 6:00 p.m. to 6:00 a.m.) and given access to Purina rodent chow and water ad libitum. On day 1, tail blood samples are taken at 8:00 am and plasma glucose levels are determined. The animals are randomly assigned to the control and compound groups. The means of plasma glucose values of the groups were matched. Animals are then orally dosed with vehicle (0.5% carboxymethyl-cellulose with 0.2% Tween-80) or compounds (at 30 mg/kg) in vehicle. The mice are dosed daily for a total of 3 days. On day 4, basal blood samples are taken. The plasma samples are analyzed for glucose concentrations using a YS12700 Dual Channel Biochemistry Analyzer (Yellow Springs Instrument Co., Yellow Springs, Ohio) and insulin concentrations using an ELISA assay.

Illustrative of the invention, the compound of Example 1 demonstrates an $EC_{50}$ of about 27 nM in the PPARα receptor binding assay, an $EC_{50}$ of about 23 nM in the PPARγ receptor binding assay, and an $EC_{50}$ of about 173 nM in the PPARδ receptor binding assay; the compound of Example 5–10 demonstrates an $EC_{50}$ of about 3 nM in the PPARα receptor binding assay, an EC$_{50}$ of about 3 nM in the PPARγ receptor binding assay, and an EC$_{50}$ of about 1250 nM in the PPARδ receptor binding assay; and the compound of Example 6–39 demonstrates an EC$_{50}$ of about 7 nM in the PPARα receptor binding assay, an EC$_{50}$ of about 2 nM in the PPARγ receptor binding assay, and an EC$_{50}$ of about 1165 nM in the PPARδ receptor binding assay. Furthermore, said compounds significantly lower serum glucose and insulin levels after three days at a daily dose of about 30 mg/kg p.o. in the ob/ob mice.

The following Examples are intended to illustrate the invention and are not to be construed as being limitations thereon. Temperatures are given in degrees Centigrade. If not mentioned otherwise, all evaporations are performed under reduced pressure, preferably between about 15 and 100 mmHg (=20–133 mbar). The structure of final products, intermediates and starting materials is confirmed by standard analytical methods, e.g., microanalysis and spectroscopic characteristics, e.g., MS, IR and NMR. Abbreviations used are those conventional in the art.

EXAMPLE 1

(R)-1-{4-[3-(4-Phenoxy-2-propyl-phenoxy)-propoxy]-benzenesulfonyl}-2,3-dihydro-1H-indole-2-carboxylic acid

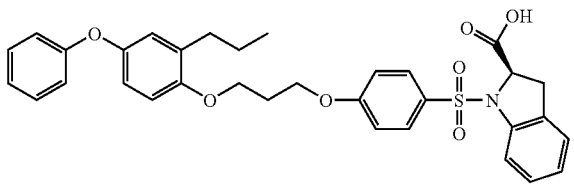

A. (R)-1-(4-Benzyloxy-benzenesulfonyl)-2,3-dihydro-11H-indole-2-carboxylic acid

To a solution of (R)-2,3-dihydro-1H-indole-2-carboxylic acid (2.89 g, 14.5 mmol) and 1N sodium hydroxide (37.7 mL, 37.7 mmol) in water (79 mL) stirring at room temperature is added dropwise a solution of 4-benzyloxybenzenesulfonyl chloride (4.1 g, 14.5 mmol) in dioxane (104 mL). Upon completion of the addition, the pH of the reaction mixture is monitored and maintained between 7–8 by slow addition of 1N aqueous sodium hydroxide over the next 2 hours. The reaction mixture is stirred overnight at room temperature. The solution is poured into crushed ice and the resulting mixture is acidified to pH 2–3 with 1N aqueous hydrochloric acid (15 mL). The product is extracted into dichloromethane (2×150 mL). The extract is washed with water (150 mL), brine (150 mL), dried over anhydrous magnesium sulfate (MgSO$_4$), filtered and concentrated to give 5.5 g of (R)-1-(4-benzyloxy-benzenesulfonyl)-2,3-dihydro-1H-indole-2-carboxylic acid as an oil: [M+1]$^+$=410.32, [M−1]$^−$=408.24.

B. (R)-1-(4-Benzyloxy-benzenesulfonyl)-2,3-dihydro-1H-indole-2-carboxylic acid methyl ester A solution of the title A compound, (R)-1-(4-benzyloxy-benzenesulfonyl)-2,3-dihydro-1H-indole-2-carboxylic acid (5.55 g, 13.6 mmol) and p-toluenesulfonic acid monohydrate (0.52 g, 2.7 mmol) in methanol (260 mL) is heated under nitrogen at reflux for 4 hours. The solution is allowed to stand overnight at room temperature which results in the formation of a crystalline solid. The crystals are collected by vacuum filtration and dried at high vacuum. A second crop of crystals is obtained from the mother liquor that is isolated and dried at high vacuum. A combined yield of 3.84 g of (R)-1-(4-benzyloxy-benzenesulfonyl)-2,3-dihydro-1H-indole-2-carboxylic acid methyl ester is obtained as a pure crystalline product: [M+1]$^+$=424.27.

C. (R)-1-(4-Hydroxy-benzenesulfonyl)-2,3-dihydro-1H-indole-2-carboxylic acid methyl ester To a suspension of the title B compound, (R)-1-(4-benzyloxy-benzenesulfonyl)-2,3-dihydro-1H-indole-2-carboxylic acid methyl ester (3.00 g, 7.1 mmol) in ethanol (200 mL) under nitrogen is added 10% palladium on carbon (0.3 g). The resulting mixture is hydrogenated at 46 psi for 18.5 hours at room temperature. The mixture is filtered through celite by vacuum filtration. The filtrate is concentrated in vacuo to give 1.31 g of (R)-1-(4-hydroxy-benzene-sulfonyl)-2,3-dihydro-1H-indole-2-carboxylic acid methyl ester which is used without further purification: [M+1]$^+$=334.22, [M−1]$^−$=332.16.

D. (R)-1-{4-[3-(4-Phenoxy-2-propyl-phenoxy)-propoxy]-benzenesulfonyl}-2,3-dihydro-1H-indole-2-carboxylic acid methyl ester To a solution of the title C compound, (R)-1-(4-Hydroxy-benzenesulfonyl)-2,3-dihydro-1H-indole-2-carboxylic acid methyl ester (1.31 g, 3.9 mmol) in N,N-dimethylformamide (50 mL) at room temperature is added anhydrous potassium carbonate (2.16 g, 15.6 mmol) in one portion. After 15 minutes, a solution of 3-(4-phenoxy-2-propyl-phenoxy)-propan-1-bromide (1.37 g, 3.9 mmol) in N,N-dimethylformamide (10 mL) is added at room temperature. The reaction mixture is stirred for 64 hours at room temperature. The reaction mixture is filtered, the filtrate is diluted with water (150 mL) and the resulting mixture is extracted with ether (2×150 mL). The organic extract is washed with water (3×100 mL) and brine (100 mL), dried over anhydrous MgSO$_4$, filtered and concentrated in vacuo to give 2.32 g of crude (R)-1-{4-[3-(4-phenoxy-2-propyl-phenoxy)-propoxy]-benzenesulfonyl}-2,3-dihydro-1H-indole-2-carboxylic acid methyl ester. Purification of the crude product by chromatography (SiO$_2$: 100 g; eluant 30%→50% ethyl acetate in hexane) afforded 1.47 g of pure (R)-1-{4-[3-(4-phenoxy-2-propyl-phenoxy)-propoxy]-benzene-sulfonyl}-2,3-dihydro-1H-indole-2-carboxylic acid methyl ester as a colorless gum: [M+1]$^+$=602.49.

E. (R)-1-{4-[3-(4-Phenoxy-2-propyl-phenoxy)-propoxy]-benzenesulfonyl}-2,3-dihydro-1H-indole-2-carboxylic acid To a mixture of the title D compound, (R)-1-{4-[3-(4-phenoxy-2-propyl-phenoxy)-propoxy]-benzenesulfonyl}-2,3-dihydro-1H-indole-2-carboxylic acid methyl ester (1.47 g, 2.44 mmol) in methanol (50 mL) under nitrogen at room temperature is added 1N aqueous sodium hydroxide (4.9 mL, 4.9 mmol) dropwise. Upon complete addition, the mixture is stirred at room temperature for 45 minutes, at which time 5 mL of tetrahydrofuran is added to facilitate the dissolution of the starting material. The mixture is stirred overnight. The reaction mixture is concentrated in vacuo, the residue is partitioned between water (50 mL) and ether (50 mL). The aqueous layer is separated and acidified with 1N aqueous hydrochloric acid. The product is extracted into dichloromethane. The extract is washed with brine, dried over anhydrous sodium sulfate (Na$_2$SO$_4$), filtered and concentrated to give 1.02 g of (R)-1-{4-[3-(4-phenoxy-2-propyl-phenoxy)-propoxy]-benzenesulfonyl}-2,3-dihydro-1H-indole-2-carboxylic acid as a white foamy solid. The solid is treated with ethanol (1 mL) which results in dissolution of the solid and upon standing crystals start to form. The crystals are separated and dried at high vacuum at 40° C. to give 0.85 g of pure (R)-1-{4-[3-(4-phenoxy-2-propyl-phenoxy)-propoxy]-benzenesulfonyl}-2,3-dihydro-1H-indole-2-carboxylic acid: [M+1]$^+$=588.46, [M−1]$^−$=586.41.

EXAMPLE 2

(R)-1-[4-(5-Methyl-2-phenyl-oxazol-4-ylmethoxy)-benzenesulfonyl]-2,3-dihydro-1H-indole-2-carboxylic acid

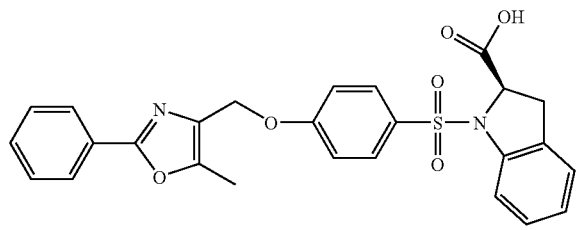

A. 4-Hydroxybenzenesulfonic Acid Disodium Salt

A solution of 4-hydroxybenzenesulfonic acid sodium salt dihydrate (20 g, 86 mmol) in 1N aqueous sodium hydroxide (86 mL, 86 mmol) is stirred and heated at 50–60° C. for 1 hour. The solution is concentrated in vacuo at 50° C. to give a solid. The solid is suspended in anhydrous toluene and concentrated in vacuo. This process is repeated twice. The solid is dried at 50° C. at high vacuum for 18 hours to give 21.34 g of 4-hydroxybenzenesulfonic acid disodium salt.

B. 4-(5-Methyl-2-phenyl-oxazol-4-ylmethoxy)-benzenesulfonic acid sodium salt

A mixture of the title A compound, 4-hydroxybenzenesulfonic acid disodium salt (3.50 g, 16.1 mmol) and 4-chloromethyl-5-methyl-2-phenyl-oxazole (4.00 g, 19.3 mmol) in 20 mL of N,N-dimethylformamide is stirred and heated under nitrogen at 110° C. for 18 hours. The cooled reaction mixture is filtered and the solid obtained is washed thoroughly with dichloromethane. The solid is dried overnight to give 1.42 g of 4-(5-methyl-2-phenyl-oxazol-4-ylmethoxy)-benzenesulfonic acid sodium salt: [M+1]$^+$=346.05, [M−1]$^−$ 32 344.02.

C. 4-(5-Methyl-2-phenyl-oxazol-4-ylmethoxy)-benzenesulfonyl chloride

To a solution of thionyl chloride (8.0 mL) and 2 drops of N,N-dimethylformamide stirring under nitrogen at 0° C. is added the title B compound, 4-(5-methyl-2-phenyl-oxazol-4-ylmethoxy)-benzenesulfonic acid sodium salt (1.42 g, 3.8 mmol) in one portion. The resulting suspension is stirred at 0° C. for 10 minutes. The ice bath is removed and the suspension is stirred at room temperature for 1.5 hours. Three more drops of N,N-dimethyl-formamide is added, after which a clear solution results upon stirring for an additional hour. The solution is concentrated under vacuo to a solid residue. The residue is partitioned between water (20 mL) and ethyl acetate (20 mL). The organic layer is separated and washed successively with water (3×20 mL), 0.1N aqueous sodium hydroxide (3×20 mL) and brine (20 mL). The organic layer is dried over anhydrous MgSO$_4$, filtered and concentrated in vacuo to give an oil which slowly solidifies to give 0.48 g of 4-(5-methyl-2-phenyl-oxazol-4-ylmethoxy)-benzenesulfonyl chloride: [M+1]$^+$=363.99.

D. (R)-1-[4-(5-Methyl-2-phenyl-oxazol-4-ylmethoxy)-benzenesulfonyl]-2,3-dihydro-1H-indole-2-carboxylic acid To a solution of the title C compound, (R)-2,3-dihydro-1H-indole-2-carboxylic acid hydrochloride (0.92 g, 4.6 mmol), 1N aqueous sodium hydroxide (12.0 mL, 12 mmol) and water (25 mL) at room temperature is added dropwise a solution of 4-(5-methyl-2-phenyl-oxazol-4-ylmethoxy)-benzenesulfonyl chloride (1.65 g, 4.6 mmol) in dioxane (33 mL). Upon completion of the addition, the pH of the reaction mixture is monitored and maintained between 7–8 by slow addition of 1N aqueous sodium hydroxide over the next 2 hours. The reaction mixture is stirred overnight at room temperature. The solution is poured into crushed ice and the resulting mixture is acidified to pH 2–3 with 1N aqueous hydrochloric acid (11 mL). The precipitate that forms is collected, washed with water and dried under high vacuum overnight to give 1.5 g of (R)-1-[4-(5-methyl-2-phenyl-oxazol-4-ylmethoxy)-benzenesulfonyl]-2,3-dihydro-1H-indole-2-carboxylic acid: [M+1]$^+$=491.2, [M−1]$^−$=489.1

EXAMPLE 3

(R)-1-[4-(5-Methyl-2-phenyl-oxazol-4-ylmethylsulfanyl)-benzenesulfonyl]-2,3-dihydro-1H-indole-2-carboxylic acid

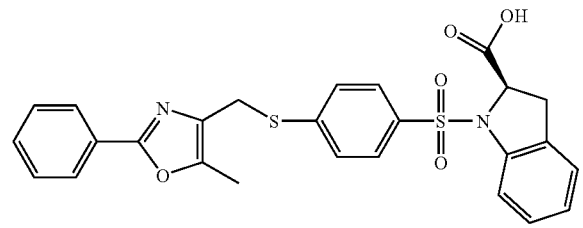

A. 4,4'-Dithiobisbenzenesulfonic Acid

To a solution of phenyl disulfide (4.36 g, 20 mmol) in dichloromethane (40 mL) at 0° C. is added a solution of chlorosulfonic acid (4.64 g, 2.95 mL, 40 mmol) in dichloromethane (60 mL) dropwise. The mixture is stirred at 0° C. for 1 hour followed by 1.5 hours at room temperature. The reaction mixture is concentrated to dryness in vacuo and the residue is partitioned between diethyl ether and water. The water phase is separated, made basic with 2N aqueous sodium hydroxide and concentrated in vacuo to half the volume. The resulting solution is refrigerated overnight. The precipitate formed overnight is discarded, the filtrate is concentrated further in vacuo until a solid started to appear. The mixture is placed in the refrigerator for 2 hours. The mixture is treated with ethanol, the solid formed is filtered, washed with ethanol twice and dried under high vacuum overnight at room temperature to give 6.0 g of 4,4'-dithiobisbenzenesulfonic acid as a white solid: [M−1]$^−$=398.8.

B. 4,4'-Dithiobisbenzenesulfonyl chloride

To thionyl chloride (70 mL) at 0° C. is added the title A compound, 4,4'-dithiobis-benzenesulfonic acid (5.9 g, 14 mmol) portionwise followed by N,N-dimethylformamide (1.4 mL). The resulting mixture is stirred at room temperature for 5 hours. The reaction mixture is concentrated to dryness in vacuo and treated with ethyl acetate followed by ice and water. The organic phase is separated, washed with water, saturated sodium bicarbonate and brine, dried over sodium sulfate and concentrated in vacuo to give 4.0 g of 4,4'-dithiobisbenzenesulfonyl chloride as a tan solid.

C. 4,4'-Dithiobis-[(R)-1-benzenesulfonyl-2,3-dihydro-1H-indole-2-carboxylic acid]

To a solution of (R)-2,3-dihydro-1H-indole-2-carboxylic acid hydrochloride (4.35 g, 21.7 mmol), 1N aqueous sodium hydroxide (43.5 mL, 43.5 mmol) and water (20 mL) at 0° C. is added dropwise a solution of the title B compound, 4,4'-dithiobisbenzenesulfonyl chloride (3.0 g, 7.24 mmol) in dioxane (60 mL). Upon completion of the addition, the pH of the reaction mixture is monitored and maintained between 7–8 by slow addition of 1N aqueous sodium hydroxide over the next 2 hours. The reaction mixture is stirred overnight at room temperature. The reaction mixture is filtered, the filtrate is poured into crushed ice and the resulting mixture is acidified to pH 2–3 with 1N aqueous hydrochloric acid. The mixture is extracted with ethyl acetate, the organic phase is washed with 1N aqueous hydrochloric acid, water, brine and dried over sodium sulfate and concentrated in vacuo to give 4.0 g of 4,4'-dithiobis-(1-benzenesulfonyl-2,3-dihydro-1H-indole-2-carboxylic acid) as a foamy solid: [M−1]⁻=667.25.

D. (R)-1-(4-Mercapto-benzenesulfonyl)-2,3-dihydro-1H-indole-2-carboxylic acid

To a solution of sodium borohydride (0.185 g, 4.86 mmol) in ethanol (60 mL) at 0° C. is added the title C compound, 4,4'-dithiobis-(1-benzenesulfonyl-2,3-dihydro-1H-indole-2-carboxylic acid) (0.65 g, 0.973 mmol) portionwise. The reaction mixture is stirred at room temperature overnight. The mixture is treated with ice/water, acidified with 2N aqueous hydrochloric acid and extracted into ethyl acetate. The combined organic extracts are washed with water and brine, dried over sodium sulfate and concentrated in vacuo to give 0.63 g of (R)-1-(4-mercapto-benzenesulfonyl)-2,3-dihydro-1H-indole-2-carboxylic acid as a gum: [M−1]= 333.9.

E. (R)-1-[4-(5-Methyl-2-phenyl-oxazol-4-ylmethylsulfanyl)-benzenesulfonyl]-2,3-dihydro-1H-indole-2-carboxylic acid To a solution of the title D compound, (R)-1-(4-mercapto-benzenesulfonyl)-2,3-dihydro-1H-indole-2-carboxylic acid (0.56 g, 1.67 mmol) in dioxane (8 mL) is added 1N aqueous sodium hydroxide (3.4 mL) and water (2 mL) at room temperature. The resulting solution is treated dropwise with a solution of 4-chloromethyl-5-methyl-2-phenyl-oxazole (0.423 g, 2.04 mmol) in dioxane (4 mL). After stirring 1.5 hours, the reaction mixture is concentrated to near dryness in vacua. The residue is taken into water, the aqueous phase is washed with ether, acidified with 2N aqueous hydrochloric acid and extracted into ethyl acetate. The combined organic phases are washed with water, brine and dried over sodium sulfate. The organic phase is concentrated in vacuo and dried overnight at high vacuum to give 0.68 g of (R)-1-[4-(5-methyl-2-phenyl-oxazol-4-ylmethylsulfanyl)-benzenesulfonyl]-2,3-dihydro-1H-indole-2-carboxylic acid as gum: [M−1]⁻=504.9.

EXAMPLE 4

The following compounds are prepared analogously to Example 1 by treating the title C compound in Example 1 with the appropriate alkylating agent, or by following the protocol described in Examples 2 or 3:

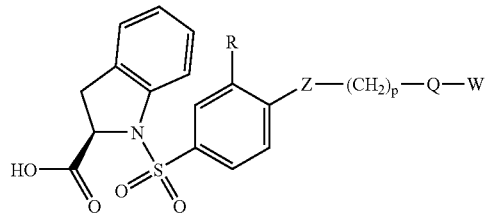

| Compd | R | Z | p | Q | W | MS [m/z] |
|---|---|---|---|---|---|---|
| 4-1 | H | O | 5 | O | ![di-tert-butylbenzyl] | 620.1 [M − 1]⁻ |
| 4-2 | H | O | 4 | O | as above | 606.48 [M − 1]⁻ |
| 4-3 | H | O | 3 | O | as above | 592.21 [M − 1]⁻ |
| 4-4 | H | O | 2 | O | as above | 578.18 [M − 1]⁻ |
| 4-5 | H | O | 3 | O | ![tetramethyltetralin] | 562.20 [M − 1]⁻ |
| 4-6 | Cl | O | 3 | O | as above | 596.10 [M − 1]⁻ |
| 4-7 | OMe | O | 3 | O | as above | 594.37 [M + 1]⁺ |

-continued
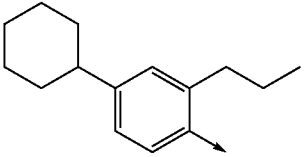
| Compd | R | Z | p | Q | W | MS [m/z] |
|---|---|---|---|---|---|---|
| 4-8 | H | O | 3 | O | 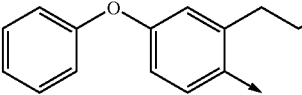 | 576.15 [M − 1]⁻ |
| 4-9 | H | O | 4 | O | 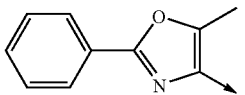 | 600.21 [M − 1]⁻ |
| 4-10 | MeO | O | 3 | O | as above | 616.30 [M − 1]⁻ |
| 4-11 | Cl | O | 3 | O | as above | 620.10 [M − 1]⁻ |
| 4-12 | n-Pr | O | 3 | O | as above |  |
| 4-13 | H | O | 2 | O | as above | 591.3 [M + 1]⁺ |
| 4-14 | H | O | 2 | a bond | 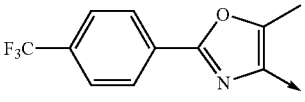 | 503.10 [M − 1]⁻ |
| 4-15 | Cl | O | 2 | a bond | as above | 537.0 [M − 1]⁻ |
| 4-16 | MeO | O | 1 | a bond | as above | 520.99 [M + 1]⁺ |
| 4-17 | Cl | O | 1 | a bond | as above | 525.04 [M + 1]⁺ |
| 4-18 | n-Pr | O | 1 | a bond | as above | 533.10 [M + 1]⁺ |
| 4-19 | H | O | 1 | a bond | 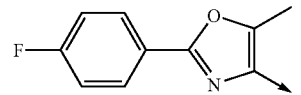 | 559.10 [M + 1]⁺ |
| 4-20 | H | S | 1 | a bond | as above | 575.29 [M + 1]⁺ |
| 4-21 | H | O | 1 | a bond | 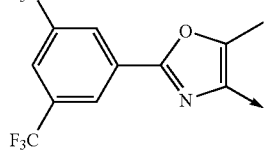 | 507.0 [M − 1]⁻ |
| 4-22 | H | S | 1 | a bond | as above | 525.36 [M + 1]⁺ |
| 4-23 | H | O | 1 | a bond |  | 626.94 [M + 1]⁺ |
| 4-24 | H | S | 1 | a bond | as above | 642.90 [M + 1]⁺ |

EXAMPLE 5

The following compounds are prepared analogously to the previous examples:

| Compd | R | Z | p | Q | W | MS [m/z] |
|---|---|---|---|---|---|---|
| 5-1 | H | O | 5 | O | 2,4-di-tert-pentylphenyl | 557.97 [M − 1]⁻ |
| 5-2 | H | O | 4 | O | as above | 544.28 [M − 1]⁻ |
| 5-3 | H | O | 3 | O | as above | 529.97 [M − 1]⁻ |
| 5-4 | H | O | 2 | O | as above | 516.29 [M − 1]⁻ |
| 5-5 | H | O | 4 | O | 3-(phenoxy)-phenyl | 540.07 [M + 1]⁺ |
| 5-6 | H | O | 3 | O | as above | 526.24 [M + 1]⁺ |
| 5-7 | H | O | 3 | O | 3-phenylbenzofuran-7-yl | 548.18 [M − 1]⁻ |
| 5-8 | H | O | 3 | O | 4-cyclohexylphenyl | 514.2 [M − 1]⁻ |
| 5-9 | H | O | 2 | a bond | 5-methyl-2-phenyloxazol-4-yl | 441.16 [M − 1]⁻ |
| 5-10 | H | O | 1 | a bond | as above | 427.11 [M − 1]⁻ |
| 5-11 | H | O | 1 | a bond | 5-methyl-2-(4-trifluoromethylphenyl)oxazol-4-yl | 497.0 [M + 1]⁺ |
| 5-12 | H | O | 1 | a bond | 5-methyl-2-(4-fluorophenyl)oxazol-4-yl | 445.0 [M − 1]⁻ |
| 5-13 | H | O | 1 | a bond | 5-methyl-2-(3,5-bis(trifluoromethyl)phenyl)oxazol-4-yl | 562.98 [M − 1]⁻ |

EXAMPLE 6

The following compounds are prepared analogously to previous examples or using methods described herein:

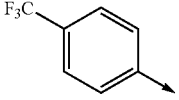

| Compd | R | Z | p | Q | W | MS [m/z] |
|---|---|---|---|---|---|---|
| 6-1 | H | —C(O)NH— | 1 | a bond | 4-(F₃C)-C₆H₄— | 455.22 [M − 1]⁻ |
| 6-2 | H | a bond | 2 | —C(O)NH— | 2,4-difluorophenyl | 439.04 [M + 1]⁺ |
| 6-3 | H | a bond | 2 | —C(O)NH— | 2,3-dichlorophenyl | 471.47 [M + 1]⁺ |
| 6-4 | H | a bond | 2 | —C(O)NH— | 4-(F₃C)-C₆H₄— | 471.19 [M + 1]⁺ |
| 6-5 | H | a bond | 2 | —C(O)N(cyclohexyl)— | cyclohexyl | 489.24 [M − 1]⁻ |
| 6-6 | H | a bond | 2 | —C(O)NMe— | cyclohexyl | 421.1 [M − 1]⁻ |
| 6-7 | H | a bond | 2 | | —C(O)-(indolin-1-yl) | 427.18 [M − 1]⁻ |
| 6-8 | H | a bond | 2 | | —C(O)-(1,2,3,4-tetrahydroisoquinolin-2-yl) | 441.15 [M − 1]⁻ |
| 6-9 | H | O | 2 | —NMe— | benzoxazol-2-yl | 443.96 [M − 1]⁻ |

Note: MS values are given with the m/z notation shown in the original. Substituent structures for W and Q are as drawn in the source (e.g., 4-trifluoromethylphenyl, 2,4-difluorophenyl, 2,3-dichlorophenyl, cyclohexyl, indolin-1-yl attached via —C(O)—, 1,2,3,4-tetrahydroisoquinolin-2-yl attached via —C(O)—, benzoxazol-2-yl).

-continued

| Compd | R | Z | p | Q | W | MS [m/z] |
|---|---|---|---|---|---|---|
| 6-10 | H | O | 5 | O | 2,4-di-tert-amylphenyl | 572.39 [M − 1]⁻ |
| 6-11 | H | O | 4 | O | as above | 558.43 [M − 1]⁻ |
| 6-12 | H | O | 3 | O | as above | 544.2 [M − 1]⁻ |
| 6-13 | H | O | 2 | O | as above | 530.34 [M − 1]⁻ |
| 6-14 | H | O | 3 | O | 1,1,4,4-tetramethyltetralin-6-yl | 516.2 [M + 1]⁺ |
| 6-15 | MeO | O | 3 | O | as above | 546.38 [M + 1]⁺ |
| 6-16 | Cl | O | 3 | O | as above | 550.1 [M + 1]⁺ |
| 6-17 | n-Pr | O | 3 | O | as above | 558.46 [M + 1]⁺ |
| 6-18 | H | O | 2 | O | as above | 502.0 [M + 1]⁺ |
| 6-19 | H | O | 3 | O | 5,6,7,8-tetrahydronaphthalen-2-yl | 460.2 [M + 1]⁺ |
| 6-20 | H | O | 3 | O | indan-5-yl | 446.2 [M + 1]⁺ |
| 6-21 | H | O | 3 | O | 4-(4-trifluoromethylphenoxy)phenyl | 566.0 [M + 1]⁺ |
| 6-22 | H | O | 3 | O | 4-cyclohexyl-2-propylphenyl | 528.28 [M − 1]⁻ |
| 6-23 | H | O | 4 | O | 4-phenoxy-2-propylphenyl | 554.13 [M + 1]⁺ |
| 6-24 | H | O | 3 | O | as above | 540.07 [M + 1]⁺ |
| 6-25 | MeO | O | 3 | O | as above | 570.06 [M + 1]⁺ |
| 6-26 | Cl | O | 3 | O | as above | 572.27 [M + 1]⁺ |
| 6-27 | n-Pr | O | 3 | O | as above | 582.20 [M + 1]⁺ |
| 6-28 | H | O | 2 | O | as above | 526.20 [M + 1]⁺ |
| 6-29 | H | S | 3 | O | as above | 554.1 [M − 1]⁻ |
| 6-30 | H | S | 2 | O | as above | 540.2 [M − 1]⁻ |
| 6-31 | H | a bond | 3 | O | as above | 524.0 [M + 1]⁺ |

-continued

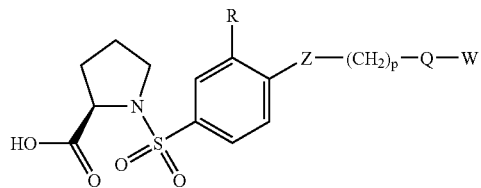

| Compd | R | Z | p | Q | W | MS [m/z] |
|---|---|---|---|---|---|---|
| 6-32 | H | O | 3 | O | 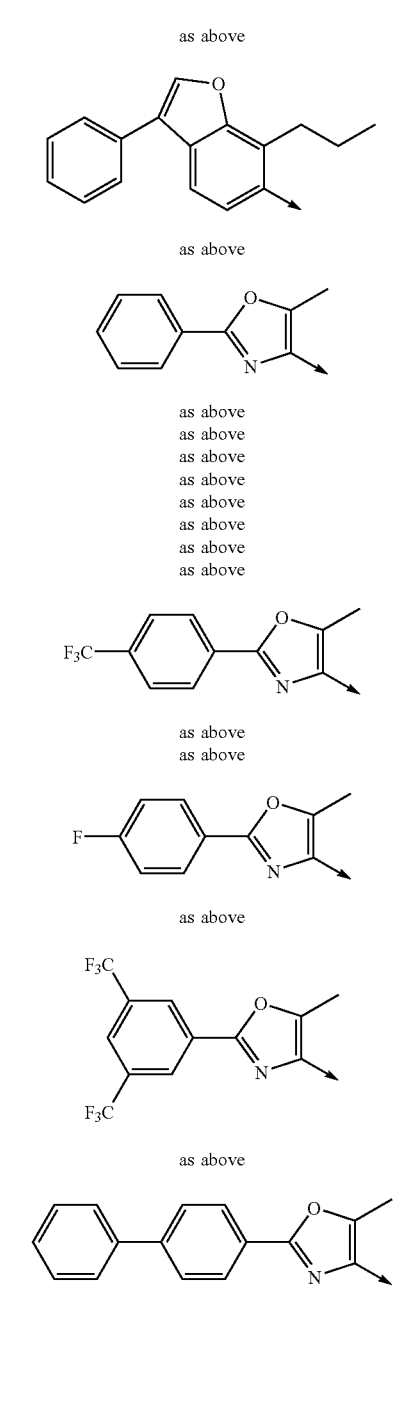 | 608.0 [M + 1]+ |
| 6-33 | H | O | 2 | O | as above | 594.0 [M + 1]+ |
| 6-34 | H | O | 3 | O | 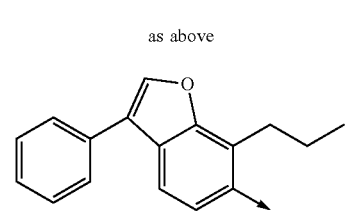 | 562.39 [M − 1]− |
| 6-35 | Cl | O | 3 | O | as above | 598.29 [M + 1]+ |
| 6-36 | H | O | 2 | a bond | 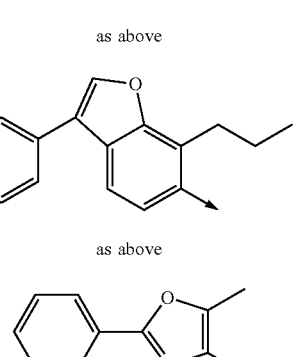 | 455.14 [M − 1]− |
| 6-37 | MeO | O | 2 | a bond | as above | 487.10 [M + 1]+ |
| 6-38 | Cl | O | 2 | a bond | as above | 491.2 [M + 1]+ |
| 6-39 | H | O | 1 | a bond | as above | 441.09 [M − 1]− |
| 6-40 | MeO | O | 1 | a bond | as above | 473.10 [M + 1]+ |
| 6-41 | Cl | O | 1 | a bond | as above | 477.0 [M + 1]+ |
| 6-42 | n-Pr | O | 1 | a bond | as above | 484.93 [M + 1]+ |
| 6-43 | H | S | 2 | a bond | as above | 471.0 [M − 1]− |
| 6-44 | H | S | 1 | a bond | as above | 459.0 [M + 1]+ |
| 6-45 | H | O | 2 | a bond | 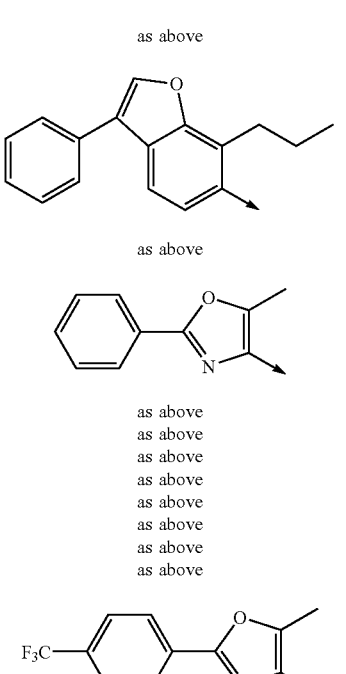 | 522.95 [M − 1]− |
| 6-46 | H | O | 1 | a bond | as above | 511.0 [M + 1]+ |
| 6-47 | H | S | 1 | a bond | as above | 527.1 [M + 1]+ |
| 6-48 | H | O | 1 | a bond | 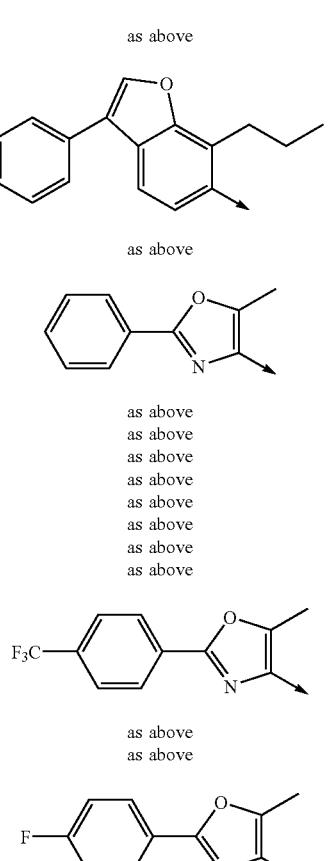 | 459.10 [M − 1]− |
| 6-49 | H | S | 1 | a bond | as above | 477.10 [M + 1]+ |
| 6-50 | H | O | 1 | a bond | 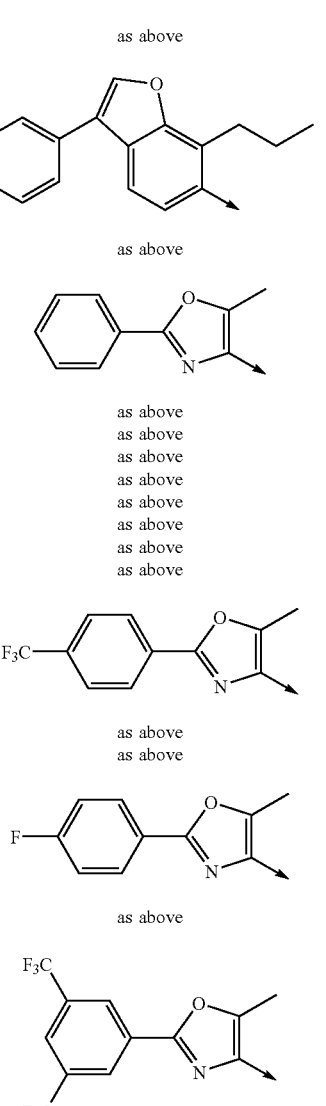 | 577.01 [M − 1]− |
| 6-51 | H | S | 1 | a bond | as above | 593.29 [M − 1]− |
| 6-52 | H | O | 1 | a bond | 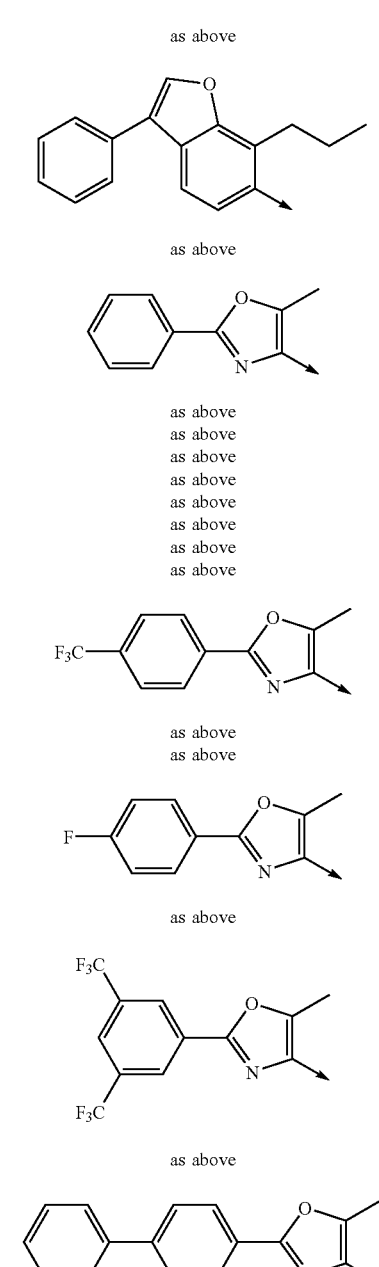 | 517.0 [M − 1]− |

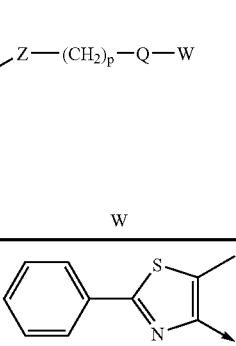

| Compd | R | Z | p | Q | W | MS [m/z] |
|---|---|---|---|---|---|---|
| 6-53 | H | O | 1 | a bond | 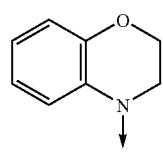 | |
| 6-54 | H | S | 2 | a bond | as above | |
| 6-55 | H | S | 1 | a bond | as above | |
| 6-56 | H | O | 2 | a bond | 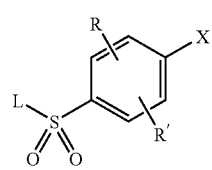 | 431.08 [M − 1]⁻ |
| 6-57 | H | O | 2 | a bond | 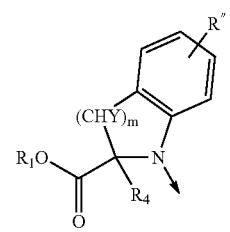 | 447.07 [M − 1]⁻ |

EXAMPLE 7

4-Chloromethyl-5-methyl-2-[4-(trifluoromethyl)phenyl]-oxazole

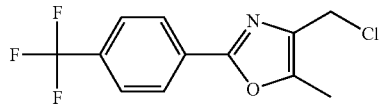

A. 4,5-Dimethyl-2-[4-(trifluoromethyl)phenyl]-oxazole 3-oxide, hydrochloride salt Into a solution of 4-trifluoromethyl benzaldehyde (400.0 g, 2.3 mol) and 2,3-butanedione monoxime (212 g, 2.055 mol) in 800 mL of glacial acetic acid at 2–5° C., hydrogenchloride gas (250 g) is slowly bubbled for 1.5 hours. The mixture is stirred at the same temperature for 1 hour further. 3.75 L of t-butyl methyl ether are added while maintaining the temperature between 5–25° C. (first 400 mL addition is exothermic). The resulting suspension is stirred for 30 minutes, then cooled to 10° C. and the solids are collected by filtration. The filter cake is washed with 500 mL of t-butylmethyl ether, and dried at 55–60° C. (20 mbar) for 18 hours to afford 550 g (91% yield) of 4,5-dimethyl-2-[4-(trifluoromethyl)phenyl]-oxazole 3-oxide, hydrochloride salt: m.p. 182–184° C. (with decomposition).

B. 4-Chloromethyl-5-methyl-2-[4(trifluoromethyl)phenyl]-oxazole

The suspension of the title A compound, 4,5-dimethyl-2-(4-trifluoromethylphenyl)-oxazole 3-oxide hydrochloride (500 g, 1.70 mol) in 4.06 L of acetonitrile is stirred for 15 minutes at room temperature, then cooled to 10° C. 491 g (3.17 mol) of POCl₃ are added at 15° C. over a period of 30 minutes. The suspension is stirred at room temperature for 16 hours, and the mixture is cooled to 10° C., and 6 L of water are added into the reaction mixture slowly (first 400 mL of water addition is very exothermic). The suspension is then stirred at room temperature for 6 hours further, and the solids are collected by filtration, washed with 2 L of water and dried to a constant weight at 50° C. (20 mbar) to afford 4-chloromethyl-5-methyl-2-[4-(trifluoromethyl)phenyl]-oxazole as a white solid (400 g, 85% yield): m.p. 97–98° C.

What is claimed is:

1. A compound of the formula

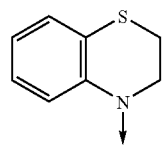

wherein

L is radical in which $R_1$ is hydrogen, optionally substituted alkyl, aryl, heteroaryl, aralkyl or cycloalkyl;

R" is hydrogen, optionally substituted alkyl, alkoxy or halogen;

m is an integer from 1 to 2;

Y is hydrogen;

$R_4$ is hydrogen; or $R_4$ and Y taken together with the carbon atoms they are attached to form a bond provided that m is 1;

R and R' are independently hydrogen, halogen, optionally substituted alkyl, alkoxy, aralkyl or heteroaralkyl; or R and R' combined together form a methylenedioxy group provided that R and R' are attached to carbon atoms adjacent to each other; or R and R' combined together with the carbon atoms they are attached to form an optionally substituted 5- to 6-membered aromatic or heteroaromatic ring provided that R and R' are attached to carbon atoms adjacent to each other; or R—C and R'—C may independently be replaced by nitrogen;

X is —Z—(CH$_2$)$_p$—Q—W wherein Z is a bond, O, S, —C(O)— or —C(O)NR$_5$— in which $R_5$ is hydrogen, alkyl or aralkyl;

p is an integer from 1 to 8;

Q is a bond provided that Z is not a bond when p is 1; or

Q is —O(CH$_2$)$_r$— or —S(CH$_2$)$_r$—, in which r is zero or an integer from 1 to 8; or Q is —O(CH$_2$)$_{1-8}$O—, —S(CH$_2$)$_{1-8}$O—, —S(CH$_2$)$_{1-8}$S—, —C(O)— or —C(O)NR$_6$— in which $R_6$ is hydrogen, optionally substituted alkyl, cycloalkyl, aryl, heteroaryl, aralkyl or heteroaralkyl;

W is cycloalkyl, aryl, heterocyclyl, aralkyl or heteroaralkyl; or

W and $R_6$ taken together with the nitrogen atom to which they are attached form a 8- to 12-membered bicyclic ring, which may be optionally substituted or may contain another heteroatom selected from oxygen, nitrogen and sulfur;

or a pharmaceutically acceptable salt thereof; or an optical isomer thereof; or a mixture of optical isomers thereof.

2. A compound according to claim 1 of the formula

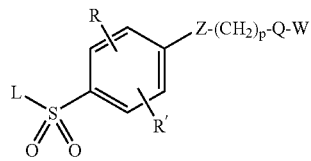

(IA)

wherein

L is

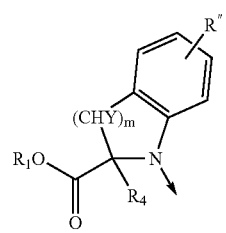

radical in which $R_1$ is hydrogen or optionally substituted alkyl;

R" is hydrogen, optionally substituted alkyl, alkoxy or halogen;

m is an integer from 1 to 2;

Y is hydrogen;

$R_4$ is hydrogen;

R and R' are independently hydrogen, halogen, optionally substituted $C_{1-6}$alkyl or $C_{1-6}$alkoxy; or R and R' combined together form a methylenedioxy group provided that R and R' are attached to carbon atoms adjacent to each other;

Z is a bond, O, S or —C(O)NR$_5$— in which $R_5$ is hydrogen, alkyl or aralkyl;

p is an integer from 1 to 5;

Q is a bond provided that Z is not a bond when p is 1; or

Q is —O(CH$_2$)$_r$— or —S(CH$_2$)$_r$— in which r is zero; or

Q is —C(O)— or —C(O)NR$_6$— in which $R_6$ is hydrogen, optionally substituted alkyl, cycloalkyl, aryl, heteroaryl, aralkyl or heteroaralkyl;

W is cycloalkyl, aryl or heterocyclyl; or

W and $R_6$ taken together with the nitrogen atom to which they are attached form a 9- to 10-membered bicyclic ring, which may be optionally substituted or may contain another heteroatom selected from oxygen, nitrogen and sulfur;

or a pharmaceutically acceptable salt thereof; or an optical isomer thereof; or a mixture of optical isomers thereof.

3. A compound according to claim 2, wherein

L is

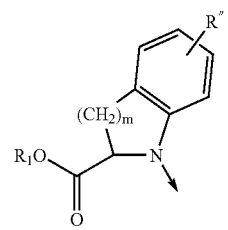

radical in which $R_1$ is hydrogen or optionally substituted alkyl;

R" is hydrogen;

m is an integer from 1 to 2;

R is hydrogen, halogen, optionally substituted $C_{1-6}$alkyl or $C_{1-6}$alkoxy;

R' is hydrogen;

Z is a bond, O or S;

p is an integer from 1 to 5;

Q is a bond provided that Z is not a bond when p is 1; or

Q is O, S or —C(O)NR$_6$— in which $R_6$ is hydrogen, optionally substituted alkyl or cycloalkyl;

W is cycloalkyl, aryl or heterocyclyl; or

W and $R_6$ taken together with the nitrogen atom to which they are attached form a 9- to 10-membered bicyclic ring, which may be optionally substituted or may contain another heteroatom selected from oxygen, nitrogen and sulfur;

or a pharmaceutically acceptable salt thereof; or an optical isomer thereof; or a mixture of optical isomers thereof.

4. A compound according to claim 3 of the formula

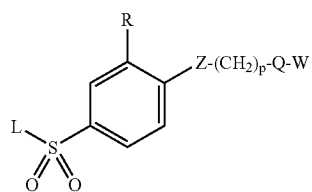

(IB)

wherein
L is

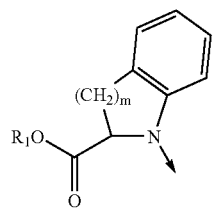

radical in which R₁ is hydrogen or optionally substituted alkyl;
m is 1;
R is hydrogen, halogen, optionally substituted $C_{1-6}$alkyl or $C_{1-6}$alkoxy;
Z is a bond, O or S;
p is an integer from 1 to 5;
Q is a bond provided that Z is not a bond when p is 1; or
Q is O, S or —C(O)NR₆— in which R₆ is hydrogen, optionally substituted alkyl or cycloalkyl;
W is cycloalkyl, aryl or heterocyclyl; or
W and R₆ taken together with the nitrogen atom to which they are attached form a 9- to 10-membered bicyclic ring, which may be optionally substituted or may contain another heteroatom selected from oxygen, nitrogen and sulfur;
or a pharmaceutically acceptable salt thereof; or an optical isomer thereof; or a mixture of optical isomers thereof.

5. A compound according to claim 4, wherein
L is

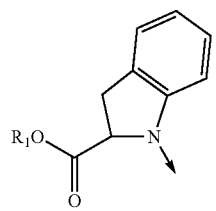

radical in which R₁ is hydrogen;
R is hydrogen, halogen, optionally substituted $C_{1-6}$alkyl or $C_{1-6}$alkoxy;
Z is a bond, O or S;
p is an integer from 1 to 4;
Q is a bond provided that Z is not a bond when p is 1; or
Q is O or S;
W is aryl or heterocyclyl;
or a pharmaceutically acceptable salt thereof; or an optical isomer thereof; or a mixture of optical isomers thereof.

6. A compound according to claim 4, wherein the asymmetric center in radical L is in the (R) configuration; or a pharmaceutically acceptable salt thereof.

7. A compound according to claim 4, wherein
R₁ is hydrogen or optionally substituted alkyl;
R is hydrogen, halogen, optionally substituted $C_{1-6}$alkyl or $C_{1-6}$alkoxy;
Z is O or S;
p is 2;
W is aryl or heterocyclyl;
or a pharmaceutically acceptable salt thereof; or an optical isomer thereof; or a mixture of optical isomers thereof.

8. A compound according to claim 7, wherein
R is hydrogen, chloro, n-propyl or methoxy;
or a pharmaceutically acceptable salt thereof; or an optical isomer thereof; or a mixture of optical isomers thereof.

9. A compound according to claim 4, wherein
R₁ is hydrogen or optionally substituted alkyl;
R is hydrogen, halogen, optionally substituted $C_{1-6}$alkyl or $C_{1-6}$alkoxy;
Z is a bond;
p is 2;
Q is a —C(O)NR₆— in which R₆ is optionally substituted alkyl;
W is aryl or heterocyclyl; or
W and R₆ taken together with the nitrogen atom to which they are attached form a 9- to 10-membered bicyclic ring, which may be optionally substituted or may contain another heteroatom selected from oxygen, nitrogen and sulfur;
or a pharmaceutically acceptable salt thereof; or an optical isomer thereof; or a mixture of optical isomers thereof.

10. A compound according to claim 9, wherein
R is hydrogen, chloro, n-propyl or methoxy;
or a pharmaceutically acceptable salt thereof; or an optical isomer thereof; or a mixture of optical isomers thereof.

11. A compound according to claim 4, wherein
R₁ is hydrogen or optionally substituted alkyl;
R is hydrogen, halogen, optionally substituted $C_{1-6}$alkyl or $C_{1-6}$alkoxy;
Z is a bond, O or S;
p is an integer from 2 to 3;
Q is O or S;
W is aryl or heterocyclyl;
or a pharmaceutically acceptable salt thereof; or an optical isomer thereof; or a mixture of optical isomers thereof.

12. A compound according to claim 11, wherein
R is hydrogen, chloro, n-propyl or methoxy;
or a pharmaceutically acceptable salt thereof; or an optical isomer thereof; or a mixture of optical isomers thereof.

13. A compound according to claim 11, wherein W is selected from the group consisting of:

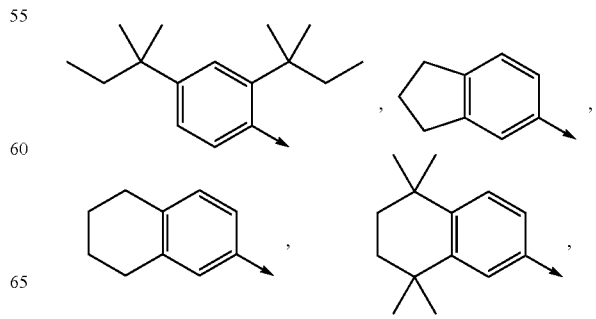

-continued

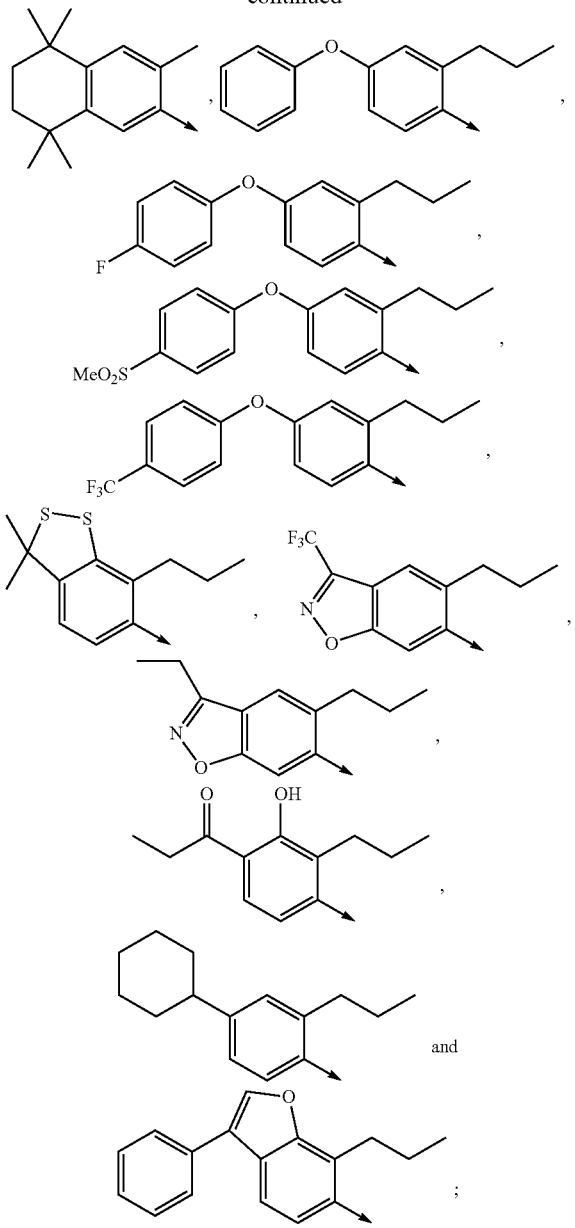

or a pharmaceutically acceptable salt thereof; or an optical isomer thereof; or a mixture of optical isomers thereof.

14. A compound according to claim 4, wherein
   $R_1$ is hydrogen or optionally substituted alkyl;
   R is hydrogen, halogen, optionally substituted $C_{1-6}$alkyl or $C_{1-6}$alkoxy;
   Z is O or S;
   p is an integer from 1 to 2;
   Q is a bond;
   W is aryl or heterocyclyl;
or a pharmaceutically acceptable salt thereof; or an optical isomer or a mixture of optical isomers thereof.

15. A compound according to claim 14, wherein
   R is hydrogen, chloro, n-propyl or methoxy;
or a pharmaceutically acceptable salt thereof; or an optical isomer thereof; or a mixture of optical isomers thereof.

16. A compound according to claim 14, wherein W is selected from the group consisting of:

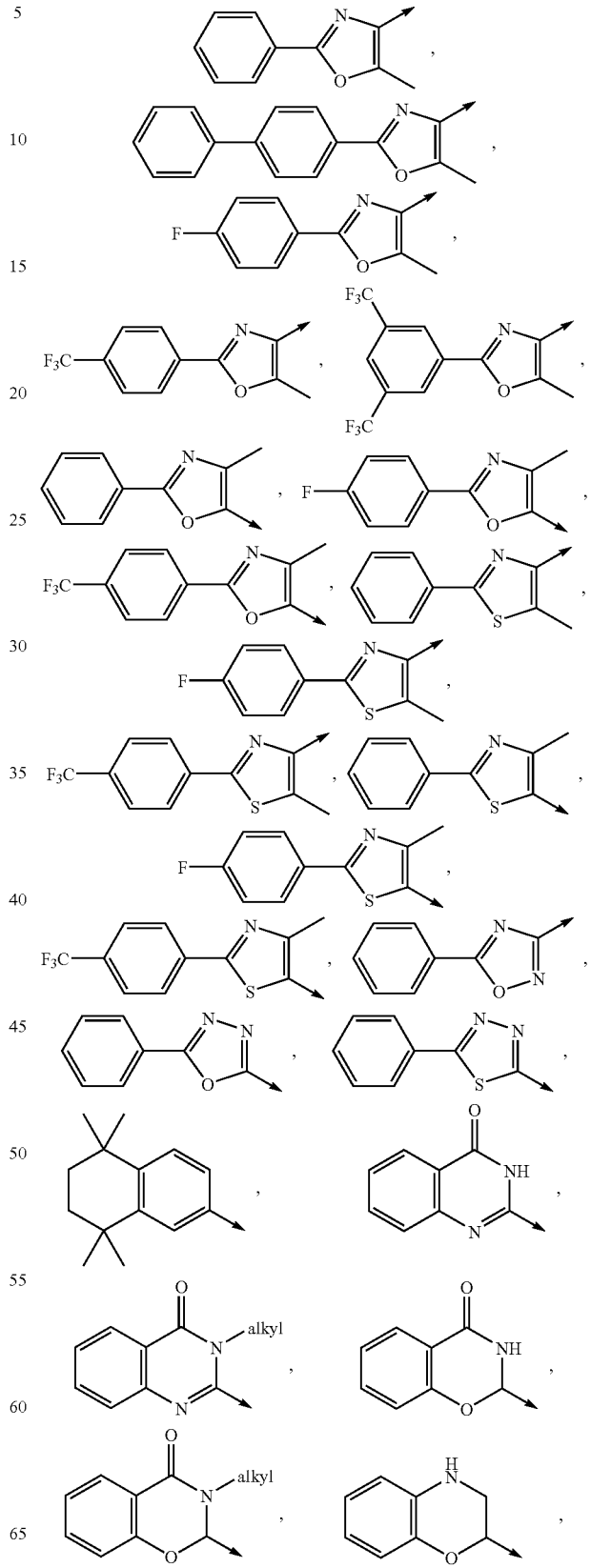

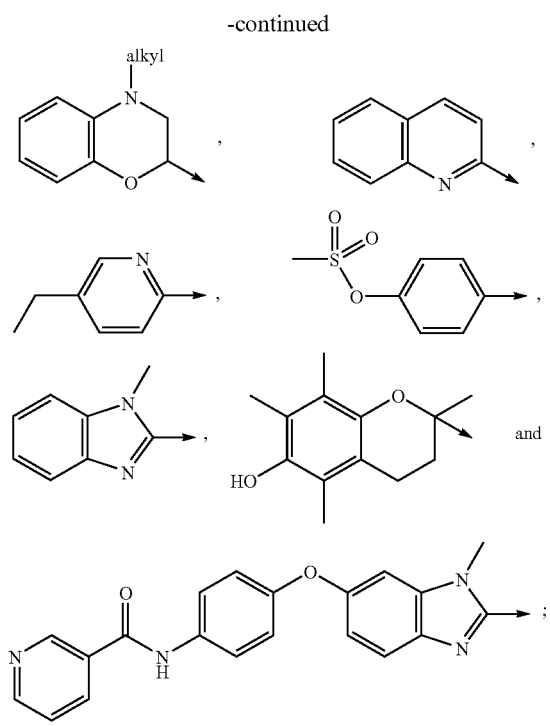

or a pharmaceutically acceptable salt thereof; or an optical isomer thereof; or a mixture of optical isomers thereof.

17. A compound according to claim 14, wherein $R_1$ is hydrogen or optionally substituted alkyl;

R is hydrogen, halogen, optionally substituted $C_{1-6}$alkyl or $C_{1-6}$ alkoxy;

Z is O or S;

p is 2;

Q is a bond;

W is selected from the group consisting of:

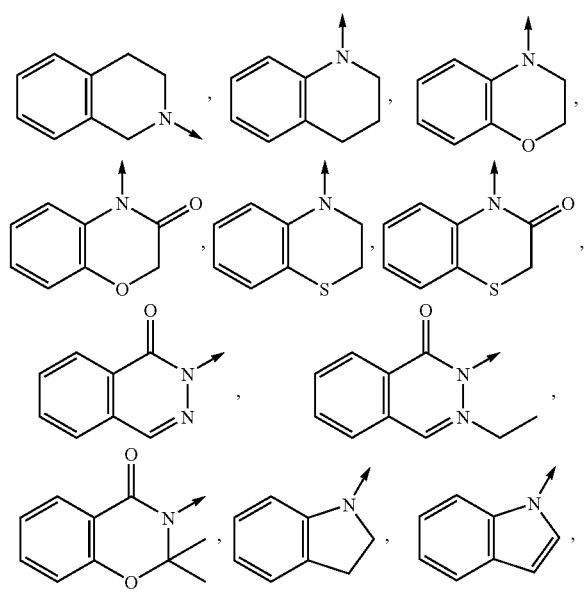

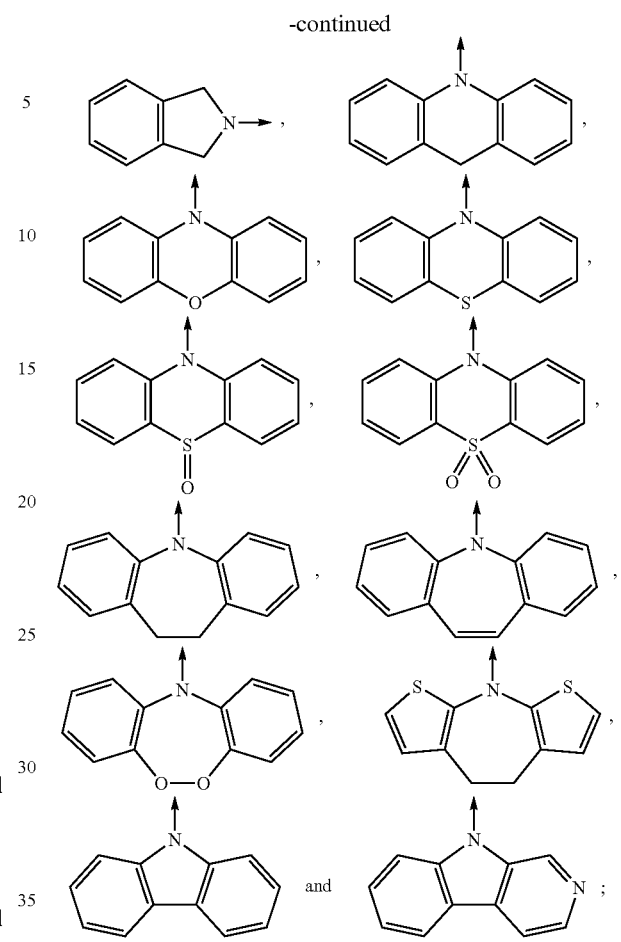

or a pharmaceutically acceptable salt thereof; or an optical isomer thereof; or a mixture of optical isomers thereof.

18. A compound according to claim 1, which is selected from the group consisting of:

(R)-1-{4-[4-(4-Phenoxy-2-propyl-phenoxy)-butoxy]-benzenesulfonyl}-2,3-dihydro-1H-indole-2-carboxylic acid;

(R)-1-{4-[3-(4-Phenoxy-2-propyl-phenoxy)-propoxy]-benzenesulfonyl}-2,3-dihydro-1H-indole-2-carboxylic acid;

(R)-1-{4-[2-(4-Phenoxy-2-propyl-phenoxy)-ethoxy]-benzenesulfonyl}-2,3-dihydro-1H-indole-2-carboxylic acid;

(R)-1-{3-Methoxy-4-[3-(4-phenoxy-2-propyl-phenoxy)-propoxy]-benzenesulfonyl}-2,3-dihydro-1H-indole-2-carboxylic acid;

(R)-1-{3-Chloro-4-[3-(4-phenoxy-2-propyl-phenoxy)-propoxy]-benzenesulfonyl}-2,3-dihydro-1H-indole-2-carboxylic acid;

(R)-1-[4-(5-Methyl-2-pheny-oxazol-4-ylmethoxy)-benzenesufonyl]-2,3-dihydro-1H-indole-2-carboxylic acid;

(R)-1-{4-[2-(4-Fluoro-phenyl)-5-methyl-oxazol-4-ylmethoxy]-benzenesulfonyl}-2,3-dihydro-1H-indole-2-carboxylic acid;

(R)-1-{4-[5-Methyl-2-(4-trifluoromethyl-phenyl)-oxazol-4-ylmethoxy]-benzenesulfonyl}-2,3-dihydro-1H-indole-2-carboxylic acid;

(R)-1-{4-[2-(3,5-Bis-trifluoromethyl-phenyl)-5-methyl-oxazol-4-ylmethoxy]-benzene-sulfonyl}-2,3-dihydro-1H-indole-2-carboxylic acid;

(R)-1-[3-Methoxy-4-(5-methyl-2-phenyl-oxazol-4-ylmethoxy)-benzenesulfonyl]-2,3-dihydro-1H-indole-2-carboxylic acid;

(R)-1-[3-Chloro-4-(5-methyl-2-phenyl-oxazol-4-ylmethoxy)-benzenesulfonyl]-2,3-dihydro-1H-indole-2-carboxylic acid;

(R)-1-[4-(5-Methyl-2-phenyl-oxazol-4-ylmethoxy)-3-propyl-benzenesulfonyl]-2,3-dihydro-1H-indole-2-carboxylic acid;

(R)-1-[4-(5-Methyl-2-phenyl-oxazol-4-ylmethylsufanyl)-benzenesufonyl]-2,3-dihydro-1H-indole-2-carboxylic acid;

(R)-1-{4-[2-(4-Fluoro-phenyl)-5-methyl-oxazol-4-ylmethylsulfanyl]-benzenesulfonyl}-2,3-dihydro-1H-indole-2-carboxylic acid;

(R)-1-{4-[5-Methyl-2-(4-trifluoromethyl-phenyl)-oxazol-4-ylmethylsulfanyl]-benzenesulfonyl}-2,3-dihydro-1H-indole-2-carboxylic acid;

(R)-1-{4-[2-(3,5-Bis-trifluoromethyl-phenyl)-5-methyl-oxazol-4-ylmethylsulfanyl]-benzenesulfonyl}-2,3-dihydro-1H-indole-2-carboxylic acid;

(R)-1-{4-[2-(5-Methyl-2-pheny}-oxazol-4-y)-ethoxy]-benzenesulfonyl-2,3-dihydro-1H-indole-2-carboxylic acid;

(R)-1-{3-Chloro-4-[2-(5-methyl-2-phenyl-oxazol-4-yl)-ethoxy]-benzenesulfonyl}-2,3-dihydro-1H-indole-2-carboxylic acid; and (R)-1-{4-[5-Methyl-2-(4-trifluoromethyl-phenyl)-oxazol-4-ylmethylsulfany]-benzene-sulfonyl}-2,3-dihydro-1H-indole-2-carboxylic acid;

or a pharmaceutically acceptable salt thereof; or an enantiomer thereof; or a mixture of enantiomers thereof.

19. A pharmaceutical composition comprising a therapeutically effective amount of a compound of claim 1 in combination with one or more pharmaceutically acceptable carriers.

* * * * *